(12) United States Patent
Bergmann et al.

(10) Patent No.: US 9,040,670 B2
(45) Date of Patent: May 26, 2015

(54) MONOCLONAL THYROID STIMULATING OR BLOCKING ANTIBODIES, PEPTIDE SEQUENCES CORRESPONDING TO THEIR VARIABLE REGIONS, AND THEIR USES IN DIAGNOSTIC, PREVENTIVE AND THERAPEUTIC MEDICINE

(75) Inventors: Andreas Bergmann, Baumlauferweg (DE); Nils G. Morgenthaler, Heiligenseestrasse (DE); Gilbert Vassart, Brussels (BE); Sabine Costagliola, Brussels (BE)

(73) Assignee: B.R.A.H.M.S GMBH, Hennigsdorg (DE)

( * ) Notice: Subject to any disclaimer, the term of this patent is extended or adjusted under 35 U.S.C. 154(b) by 969 days.

(21) Appl. No.: 13/181,170

(22) Filed: Jul. 12, 2011

(65) Prior Publication Data

US 2012/0253019 A1 Oct. 4, 2012

Related U.S. Application Data

(62) Division of application No. 11/570,951, filed as application No. PCT/EP2005/006500 on Jun. 16, 2005, now Pat. No. 8,029,790.

(30) Foreign Application Priority Data

Jun. 29, 2004 (EP) .................................. 04015239

(51) Int. Cl.
| | | |
|---|---|---|
| G01N 33/558 | (2006.01) | |
| C07K 16/28 | (2006.01) | |
| G01N 33/564 | (2006.01) | |
| G01N 33/76 | (2006.01) | |
| A61K 39/00 | (2006.01) | |

(52) U.S. Cl.
CPC ....... C07K 16/2869 (2013.01); *A61K 2039/505* (2013.01); *C07K 2316/95* (2013.01); *C07K 2316/96* (2013.01); *C07K 2317/92* (2013.01); G01N 33/564 (2013.01); G01N 33/76 (2013.01); *C07K 2317/34* (2013.01)

(58) Field of Classification Search
CPC ........... C07K 16/2869; C07K 2316/95; G01N 33/558; A61K 2039/515
USPC ...................................... 530/388.22; 435/334
See application file for complete search history.

(56) References Cited

FOREIGN PATENT DOCUMENTS

| DE | 19907094 C1 | 2/1999 |
|---|---|---|
| EP | 1301767 B1 | 7/2001 |
| WO | 95/23865 | 9/1995 |
| WO | 00/49050 | 8/2000 |
| WO | 00/61637 | 10/2000 |
| WO | 03/018632 | 3/2003 |
| WO | 2004/048415 | 6/2004 |
| WO | 2004/050708 | 6/2004 |

OTHER PUBLICATIONS

Sanders et al., "Thyroid-Stimulating Monoclonal Antibodies", Thyroid, vol. 12(12) 2002, 1043-1050.
Sanders et al., "Human Monoclonal Thyroid Stimulating Autoantibody", The Lancet, vol. 362, Jul. 12, 2003, 126-128.
Costagliola et al., "Generation of a Mouse Monoclonal TSH Receptor Antibody with Stimulating Activity", BBRC 299 (2002) 891-896.
Ando et al., "A Monoclonal Thyroid-Stimulating Antibody", The Journal of Clinical Investigation, Dec. 2002, vol. 110(11), 1667-1674.
Kosugi et al., "Identification of Thyroid-Stimulating Antibody-Specific Interaction Sites in the N-Terminal Region of the Thyrotropin Receptor", Molecular Endocrinology, 1993, vol. 7(1), 114-130.
Rapoport et al., "The Thyrotropin (TSH) Receptor: Interaction with TSH and Autoantibodies", Endocrine Reviews, Dec. 1998, vol. 19(6): 673-716.
Szkudlinski et al., "Thyroid-Stimulating Hormone and Thyroid-Stimulating Hormone Receptor Structure-Function Relationships", Physiol Rev., vol. 82, Apr. 2002, 473-502.
Smits et al., "Glycoprotein Hormone Receptors: determinants in leucine-rich repeats responsible for ligand specificity", The EMBO Journal, vol. 22(11), 2003, 2692-2703.
Kajava et al., "Modeling of the three-dimensional structure of proteins with the typical leucine-rich repeats", Structure, Sep. 15, 1995; vol. 3(9), 867-877.
Weetman, "Graves' Disease", The New England Journal of Medicine, Oct. 26, 2000, vol. 343(17), 1236-1248.
Prabhakar et al., "Current Perspective on the Pathogenesis of Graves' Disease and Opthalmopathy", Endocrine Reviews, Dec. 2003, 24(6); 802-835.
Shimojo et al., "Induction of Graves-like disease in mice by immunization with fibroblasts transfected with the thyrotropin receptor and a class II molecule", Proc. Natl. Acad. Sci., USA, vol. 93, Oct. 1996, 11074-11079.
Costagliola et al., "Genetic immunization of outbred mice with thyrotropin receptor cDNA provides a model of Graves' disease", The Journal of Clinical Investigation, Mar. 2000, vol. 105(6), 803-811.
Nagayama et al., "A Novel Murine Model of Graves' Hyperthyroidism with Intramuscular Injection of Adenovirus Expressing the Thyrotropin Receptor", The Journal of Immunology, 2002, vol. 168, 2789-2794.
Rao et al., "Contrasting Activities of Thyrotropin Receptor Antibodies in Experimental Models of Graves' Disease Induced by Injection of Transfected Fibroblasts or Deoxyribonucleic Acid Vaccination", Endocrinology 144(1), Jan. 2003, 260-266.

(Continued)

*Primary Examiner* — Lynn Bristol
(74) *Attorney, Agent, or Firm* — Heslin Rothenberg Farley & Mesiti P.C.

(57) ABSTRACT

Monoclonal antibodies (mAbs) having thyroid stimulating activity (TSAb), especially full or considerably agonistic activity, or thyroid blocking activity (TBAb), which are obtainable by genetic immunization of mice, or fragments (F(ab')$_2$, Fab or Fv) or humanized forms of such monoclonal antibodies or single chain forms (SCA; scFv) of such fragments, which antibodies, or their fragments, compete with bovine TSH for epitopes of the human TSHr, compete with autoantibodies from sera from Graves' patients as well as with autoantibodies from sera from patients harboring blocking autoantibodies for epitopes of the human TSHr, bind to conformational epitopes of the human TSHr located in the first 281 amino acids of the human TSHr, and usually also bind to TSFR receptors (TSHr) from different animals. Various uses of such antibodies, or of peptides corresponding to variable regions of such antibodies, are also described and claimed.

2 Claims, 11 Drawing Sheets

(56) References Cited

OTHER PUBLICATIONS

Figure 2:
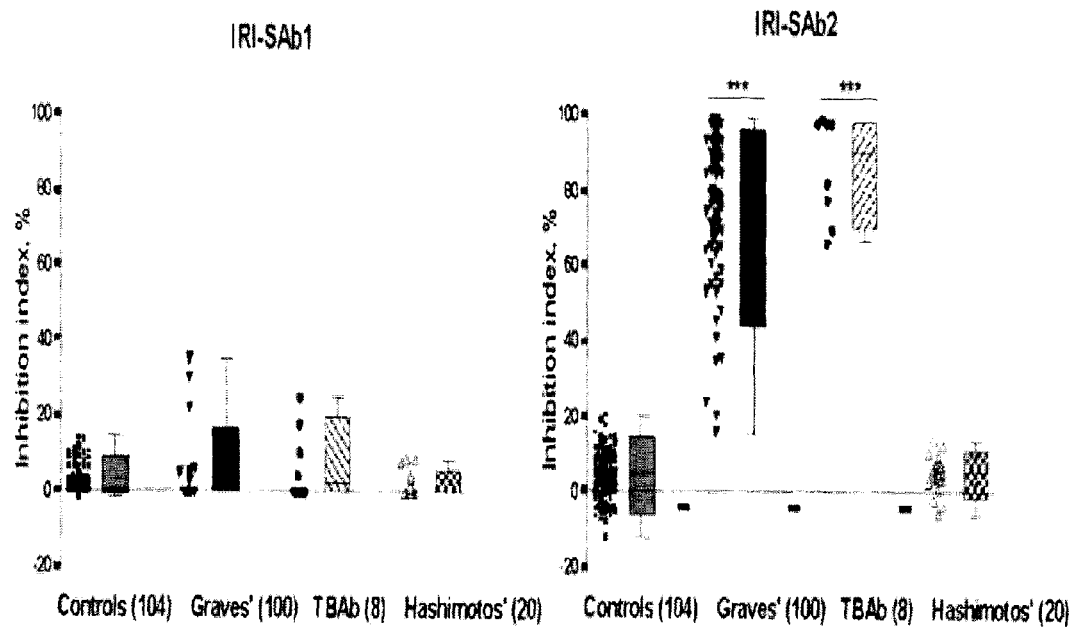
Figure 2:
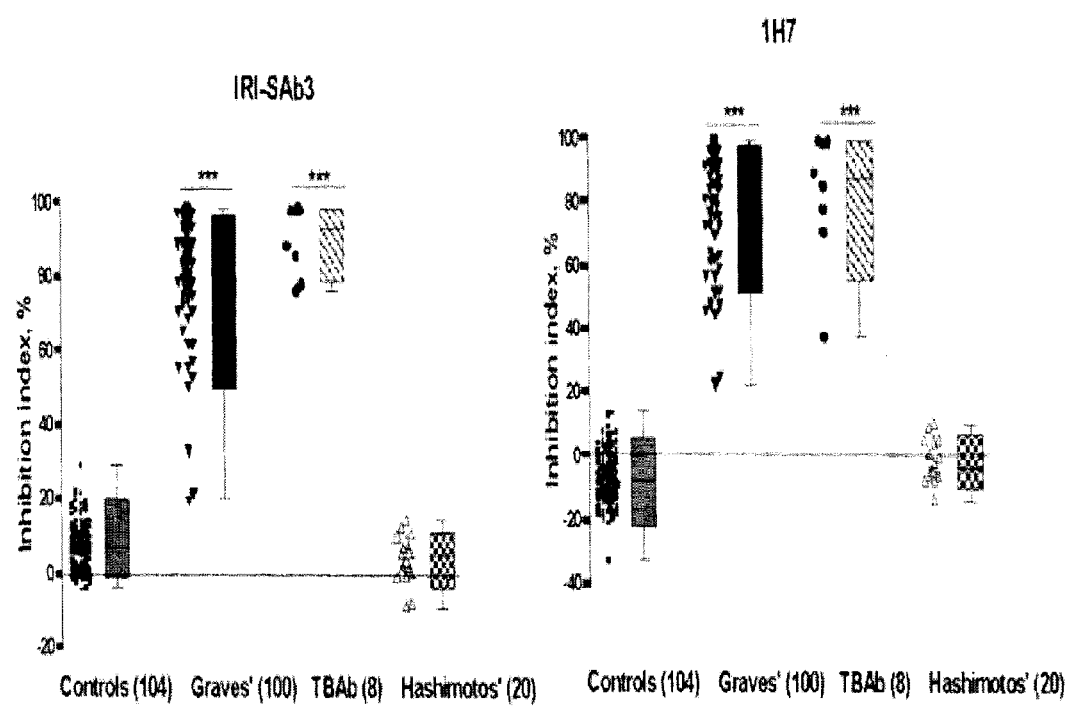
Figure 2:
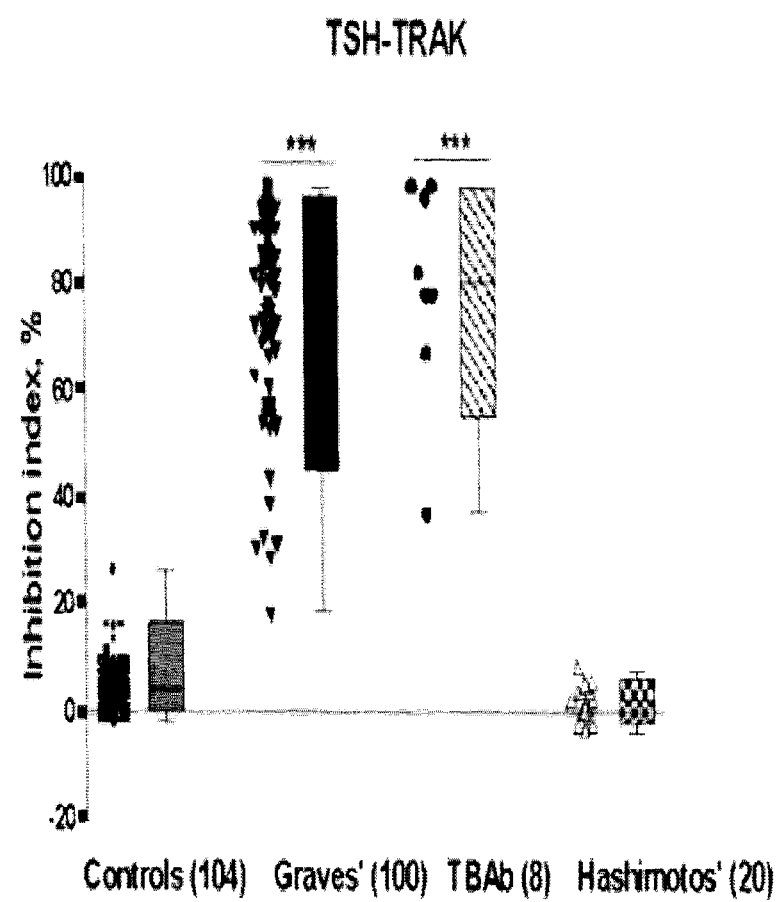

Costagliola et al., "Production of bioactive amino-terminal domain of the thyrotropin receptor via insertion in the plasma membrane by a glycosylphosphatidylinositol anchor", FEBS Letters 436 (1998), 427-433.

Perret et al., "Stable Expression of the Human Tsh Receptor in CHO Cells and Characterization of Differentially Expressing Clones", Biochemical and Biophysical Research Communications, vol. 171(3), 1990, 1044-1050.

Van Sande et al., "Thyroid stimulating immunoglobulins, like thyrotropin activate both the cyclic AMP and the PIP2 cascades in CHO cells expressing the TSH receptor", Molecular and Cellular Endocrinology, vol. 88, 1992, R1-R5.

Costagliola et al., "Second Generation Assay for Thyrotropin Receptor Antibodies Has Superior Diagnostic Sensitivity for Graves' Disease", Journal of Clinical Endocrinology and Metabolism, vol. 84(1), 1999, 90-97.

Minich et al., "Antibodies to TSH-receptor in thyroid autoimmune disease interact with monoclonal antibodies whose epitopes are broadly distributed on the receptor", Clinical and Experimental Immunology, 2004, vol. 136, 129-136.

Weiss et al., "Thyrotropin Regulation by Thyroid Hormone in Thyroid Hormone Receptor β-Deficient Mice", Endocrinology 1997, vol. 138(9), 3624-3629.

Costagliola et al., "Recombinant Thyrotropin Receptor and the Induction of Autoimmune Thyroid Disease in BALB/c Mice: A New Animal Model", Endocrinology 1994, vol. 135(5), 2150-2159.

Kettleborough et al., "Optimization of primers for cloning libraries of mouse immunoglobulin genes using the polymerase chain reaction", Eur. J. Immunol. 1993, vol. 23, 206-211.

Jukes et al., "Evolutionary nucleotide replacements in DNA", Nature vol. 281, Oct. 18, 1979, 605-606.

Chazenbalk et al., "A Mouse Monoclonal Antibody to a Thyrotropin Receptor Ectodomain Variant Provides Insight into the Exquisite Antigenic Conformational Requirement, Epitopes and in Vivo Concentration of Human Autoantibodies", Journal of Clinical Endocrinology and Metabolism, vol. 84(2), 1999, 702-710.

Cornelis et al., "Purification and Characterization of a Soluble Bioactive Amino-Terminal Extracellular Domain of the Human Thyrotropin Receptor", Biochemistry 2001, vol. 40(33), 9860-9869.

Jaume et al., "Thyrotropin Receptor Autoantibodies in Serum Are Present at Much Lower Levels Than Thyroid Peroxidase Autoantibodies: Analysis by Flow Cytometry", Journal of Clinical Endocrinology and Metabolism, 1997, vol. 82(2), 500-507.

Kasagi et al., "Mechanisms of increased sensitivity for detection of thyroid stimulating antibodies by use of hypotonic medium", Acta Endocrinologica (Copenh) 1989, vol. 121, 216-222.

Smith et al., "Autoantibodies to the Thyrotropin Receptor", Endocrine Reviews 1988, vol. 9(1), 106-121.

Libert et al., "Cloning, Sequencing and Expression of the Human Thyrotropin (TSH) Receptor: Evidence for Binding of Autoantibodies", Biochemical and Biophysical Research Communications, vol. 165(3), 1989, 1250-1255.

Nagayama et al., "Molecular Cloning, Sequence and Functional Expression of the cDNA for the Human Thyrotropin Receptor", Biochemical and Biophysical Research Communications, 1989, vol. 165(3), 1184-1190.

Rapoport et al., "Thyroid Autoantibodies in Graves' disease". In Graves' Disease Pathogenesis and Treatment, 2000, Rapoport and McLachlan, editors, Kluwer Academic Publishers, Boston. 43-66.

Vieira et al., "The half-lives of serum immunoglobulins in adult mice", Eur. J. Immunol. 1998, vol. 18, 313-316.

Gura, 2002, "Therapeutic antibodies: Magic bullets hit the target", Nature 417, 584-586.

Pacini et al., "Recombinant Human Thyrotropin-Stimulated Serum Thyroglobulin Combined with Neck Ultrasonography has the Highest Sensitivity in Monitoring Differentiated Thyroid Carcinoma", The Journal of Clinical Endocrinology & Metabolism 2003, 88(8), 3668-3673.

International Search Report for priority application, PCT International Patent Application No. PCT/EP2005/006500.

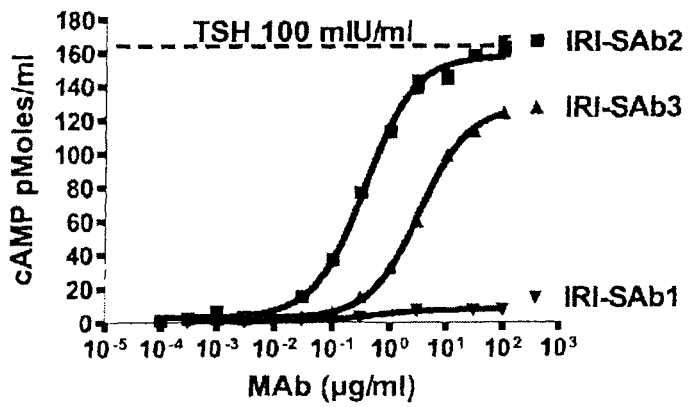
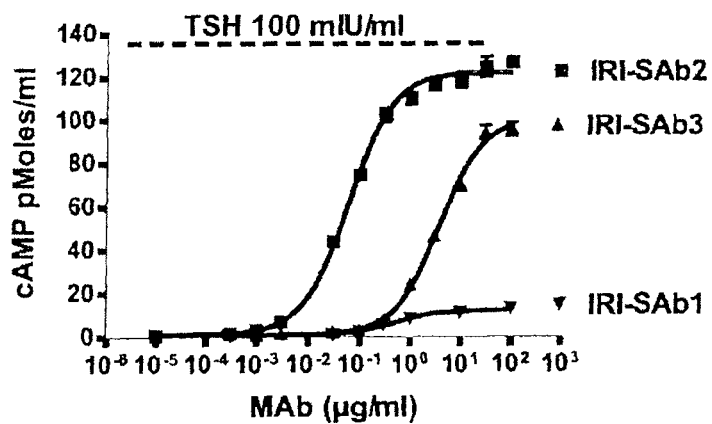
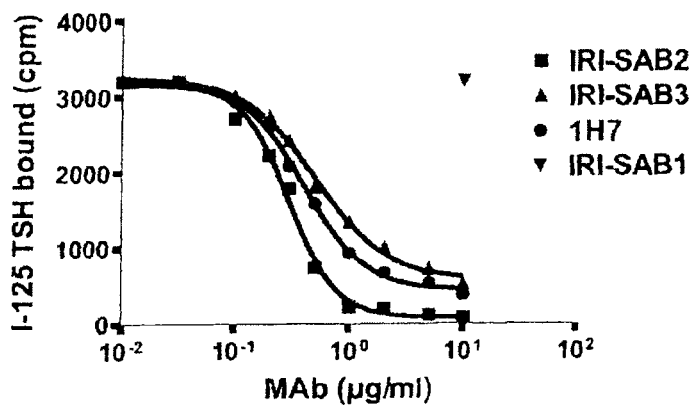
FIGURE 1

A

Epitope IRI-SAb2

|    | LRR1 | LRR2 | LRR3 | LRR4 | LRR5 | LRR6 | LRR7 | LRR8 | LRR9 |
|----|------|------|------|------|------|------|------|------|------|
| X1 | Q55  | S79  | T104 | K129 | F154 | L180 | D203 | S229 | K250 |
| X2 | T56  | R80  | H105 | F130 | I155 | T181 | A204 | L230 | E251 |
| L  |      |      |      |      |      |      |      |      |      |
| X3 | K58  | Y82  | E107 | G132 | E157 | K183 | Y206 | D232 | I253 |
| L  |      |      |      |      |      |      |      |      |      |
| X4 | I60  | S84  | R109 | F134 | T159 | Y185 | N208 | S234 | R255 |
| X5 | E61  | I85  | N110 | N135 | D160 | N186 | K209 | Q235 | N256 |

B

Epitope IRI-SAb3

|    | LRR1 | LRR2 | LRR3 | LRR4 | LRR5 | LRR6 | LRR7 | LRR8 | LRR9 |
|----|------|------|------|------|------|------|------|------|------|
| X1 | Q55  | S79  | T104 | K129 | F154 | L180 | D203 | S229 | K250 |
| X2 | T56  | R80  | H105 | F130 | I155 | T181 | A204 | L230 | E251 |
| L  |      |      |      |      |      |      |      |      |      |
| X3 | K58  | Y82  | E107 | G132 | E157 | K183 | Y206 | D232 | I253 |
| L  |      |      |      |      |      |      |      |      |      |
| X4 | I60  | S84  | R109 | F134 | T159 | Y185 | N208 | S234 | R255 |
| X5 | E61  | I85  | N110 | N135 | D160 | N186 | K209 | Q235 | N256 |

C

Epitope 1H7

|    | LRR1 | LRR2 | LRR3 | LRR4 | LRR5 | LRR6 | LRR7 | LRR8 | LRR9 |
|----|------|------|------|------|------|------|------|------|------|
| X1 | Q55  | S79  | T104 | K129 | F154 | L180 | D203 | S229 | K250 |
| X2 | T56  | R80  | H105 | F130 | I155 | T181 | A204 | L230 | E251 |
| L  |      |      |      |      |      |      |      |      |      |
| X3 | K58  | Y82  | E107 | G132 | E157 | K183 | Y206 | D232 | I253 |
| L  |      |      |      |      |      |      |      |      |      |
| X4 | I60  | S84  | R109 | F134 | T159 | Y185 | N208 | S234 | R255 |
| X5 | E61  | I85  | N110 | N135 | D160 | N186 | K209 | Q235 | N256 |

FIGURE 4

VH

```
                         24   CDR1   35            49   CDR2    61
IRI-SAb2  AY60795ᴬ .SCRASGYSFTAYTMNWVKQSHGKNLEWIGLINPNNGGTNYNQKF
IRI-SAb3  AY60797  .SCRASGYSFTAYTMNWVKQSHGYNLEWIGLINPNNGGANYNQKF
1H7       AY60799  .SCKTSGYTFTSYWMHWVKQRPGQGLEWIGEIDPSDSYSNYNQKF

IRI-SAb2           EGKATLTVDKSSTTAYMELLSLTSEDSAVYYCARRVWD..YFDYW
IRI-SAb3           KGKATLTVDKSSSTAYMELLSLTSEDSAVYYCARRVWD..YFDYW
1H7                KGKATLTVDKSSSTAYMQLSSLTSEDSAVYYCARNYGSGYYFDYW
                                                       CDR3

IRI-SAb2           GQGTSLTVSS..........
IRI-SAb3           GQGTTLTVSS..........
1H7                GQGTTLTVSS..........
```

VL

```
                          CDR1               CDR2
                         25     34          50   56
IRI-SAb2  AY60796  .EGSITCKASQNVGTNVAWYQQKGGQSLELLIYGASNRHTGVPDR
IRI-SAb3  AY60798  .EGSITCKASQNVGTNVAWYQQKVGQSLELLIYGASSRHTGVPDR
1H7       AY607100 .KVTMTCSASSSVS YMHWYQQKSGTSPKRWIYDTSKLASGVPAR 89    97
IRI-SAb2           FTGRGSGTDFTLTITNVQSEDMTNYCEQYSRYPLTFGAG..
IRI-SAb3           FTGSGSGTDFTLTITDVQSEDMTNYCEQYSSYPLTFGAG..
1H7                FSGSGSGTSYSLTISSMEAEDAATYYCQQWSSNPYTFGGG..
                                                   CDR3
```

FIGURE 5

Figure 7:
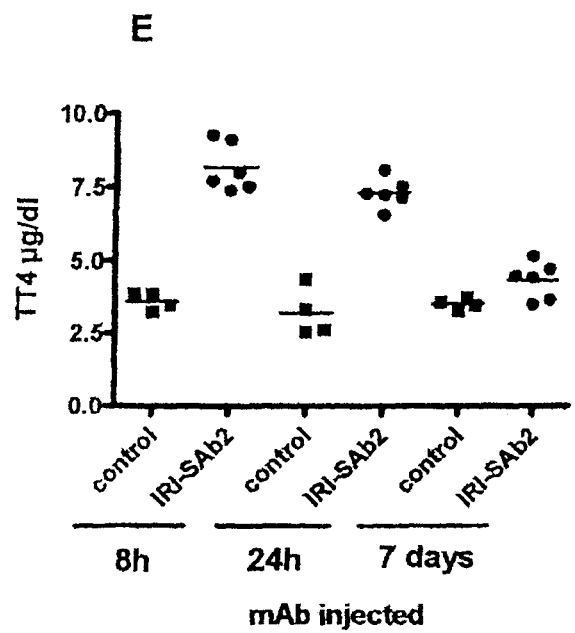

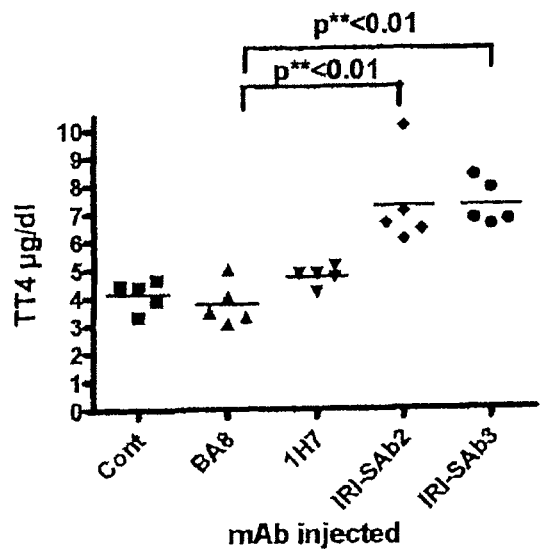
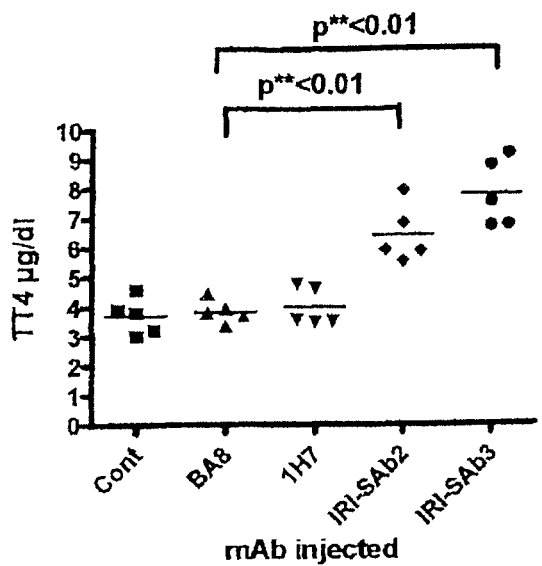
FIGURE 7

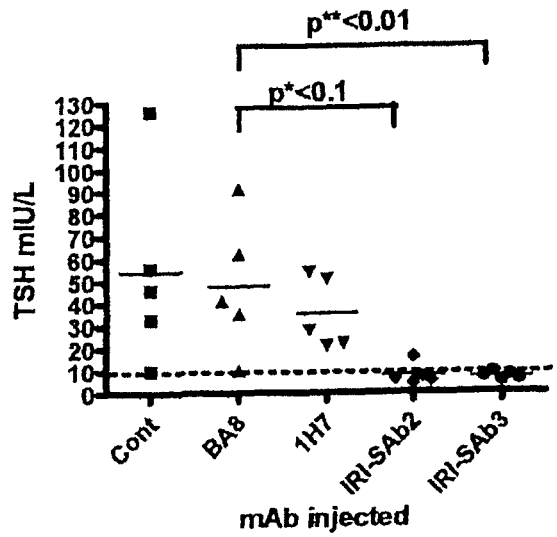
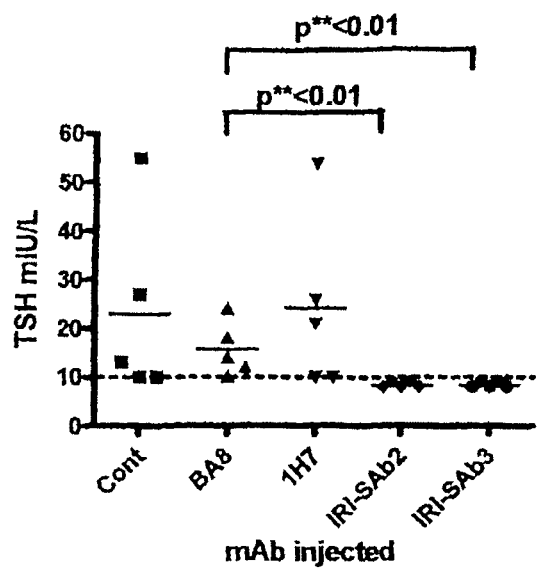
FIGURE 7

MONOCLONAL THYROID STIMULATING OR BLOCKING ANTIBODIES, PEPTIDE SEQUENCES CORRESPONDING TO THEIR VARIABLE REGIONS, AND THEIR USES IN DIAGNOSTIC, PREVENTIVE AND THERAPEUTIC MEDICINE

CROSS REFERENCE TO RELATED APPLICATIONS

This application is a divisional of U.S. Application No. 11/570,951, submitted Dec. 19, 2006, now issued as U.S. 8,029,790, which is a §371 filing of PCT International Application PCT/EP2005/006500, filed Jun. 16, 2005 and published in English as WO2006/002774 on Jan. 12, 2006, which claims the priority of European Application No. 04015239.9 filed Jun. 29, 2004. The entire contents of each of these applications and all other patents, published applications and other references cited herein are hereby incorporated by reference into the present application.

The present invention relates to new monoclonal antibodies (mAb) recognizing the thyrotropin receptor (TSHr) and having stimulating or blocking activities, to characteristic amino acid sequences and other features of said new mAbs, and to various uses of such mAbs or their specifically binding fragments in medicine, as well as uses in related fields conceivable in view of the disclosed exact information regarding their binding behaviour and structural and sequential features.

Together with the lutropin/choriogonadotropin (LH/CGr) and follitropin (FSHr) receptors, the thyrotropin receptor (TSHr) constitute the glycoprotein hormone receptor subfamily (GPHR), themselves members of the large family of rhodopsin-like G protein-coupled receptors (GPCR). GPHRs harbour a large N-terminal extracellular domain, responsible for the specificity of hormone recognition and binding, and a heptahelical transmembrane region it shares with all GPCRs. This "serpentine" portion is responsible for trans-mission of the activation signal, mainly to the G protein Gs. The extracellular domain is composed of two cysteine-rich clusters flanking nine leucine-rich repeats (LRRs). A structural model of the LRR portion of the TSHr ectodomain, based on the crystal structure of the porcine ribonuclease inhibitor (1), has been proposed. It takes the shape of a segment of a horseshoe, made of a succession of beta-strands and alpha-helices, on the concave and convex surfaces of the horseshoe, respectively. According to current knowledge, GPCRs are thought to be activated by their respective ligand (TSH, LH/CG, FSH) after interaction of the beta subunit of the hormones with specific residues of the beta-strands of the horseshoe.

In contrast to the LH/CG and FSH receptors, the TSHr can also be activated by autoantibodies directed against its ectodomain (1). This is the immediate cause of thyrotoxicosis and thyroid hyperplasia in patients with Graves' disease (5,6). After publication of the complete amino acid sequence of the human TSHr (hTSHr) and TSHr variants from other mammals, numerous antibodies were generated in different animals against the complete TSHr or its partial sequences, but for a long time antibodies having thyroid stimulating properties and being agonists of the TSHr remained elusive.

Most of the antibodies generated showed blocking activity, i.e. were able to diminish or block, in bioassays, the stimulating effect of TSH on the TSHr. Among them a few also turned out to be potent competitors of stimulating autoantibodies found in sera of patients with thyroid autoimmune diseases, especially Graves' disease. Such blocking mAbs, more specially mAbs which bind to epitopes comprising the amino acids FDSH corresponding to amino acids 381 to 384 of the human TSHr (hTSHr), are described and claimed in German Patent DE 199 07 094 C1 and corresponding WO 00/49050 A2/A3. Said patent also claims the use of blocking antibodies for the treatment of hyperthyroidism and related conditions.

After years of unsuccessful attempts, finally murine models of Graves' disease (GD) have been developed (7-10) and this has recently opened the way to the isolation of a limited number of monoclonal antibodies (mAbs) with thyroid stimulating activity (TSAb) (11-13). These mAbs were shown to stimulate the TSHr in the nanomolar range ex vivo and, when compared with bovine or human TSH, acted as partial agonists. Finally, a single human mAb with TSAb activity has recently been generated from peripheral lymphocytes of a patient with Graves disease (14). In none of these cases have the epitopes recognized by the mAbs been precisely delineated.

mAbs with TSAb activity constitute invaluable scientific tools to probe the mechanisms implicated in the intramolecular transduction of the activation signal between the ectodomain of the TSHr and other GPHRs and their serpentine domain. However, such antibodies, being potential agonists of the TSHr, also can be considered as candidates for a number of uses in diagnostic and therapeutic medicine for which, at present, TSH, either naked or labeled or in the form of conjugates, is used. One of such uses corresponds to the use of TSH, usually as recombinant TSH (e.g. as Thyrogen®, thyrotropin alfa for injection, Genzyme Therapeutics), as an adjunctive diagnostic tool for serum thyroglobulin (Tg) testing with or without radioiodine whole-body scan (WBS) in the follow-up of patients with a history of well-differentiated thyroid cancer for the presence of remnants or of residual or recurrent cancer after thyroidectomy or treatment with radioiodine.

In diagnostics, suitable antibodies which compete with pathogenic autoantibodies present in the circulation of patients affected by thyroid autoimmune diseases, or with specific populations of such autoantibodies, were already considered as potential alternatives for the conventional competitor TSH in assays for the determination of autoantibodies, more specially for labeled bovine TSH (bTSH), presently used in the overwhelming number of competitive immunoassays for the determination of autoantibodies to the TSHr (TRAb). Such uses of antibodies as competitors are, for example, disclosed in applicants' EP 1 301 767 A1 (determination of blocking autoantibodies), or PCT/EP03/12129 (WO 04/048415) disclosing inter alia the use of affinity purified labeled polyclonal human antibodies as competitors in such assays. The complete disclosure of both applications is herewith incorporated into the present application by reference. Both applications disclose that the use of antibodies as competitors compared to the use of TSH can provide certain significant advantages, e.g. with respect to a desired selectivity of a determination or to the stability of the specific binding of the competitor to TSHr preparations after extended storage of the assay kit.

To be useful as alternatives for TSH in diagnostic and therapeutic applications, mAbs preferably must bind, with the appropriate affinity, to portions of the TSHr involved in TSH binding and autoantibody binding respectively. For therapeutic or in vivo diagnostic purposes the agonistic, stimulating activity, or alternatively the blocking activity, of such mAbs preferably should be of the same order of magnitude as that of TSH and autoantibodies respectively, and it must be observable also under physiological conditions, e.g. at physiological salt concentrations.

The present invention provides, inter alia, a novel class of well-defined mAbs against the TSHr which fulfill the above requirements, and which have other properties and advantages which become apparent for a skilled person reading the following description.

The invention, therefore, according to one of its main aspects provides monoclonal antibodies (mAbs), which monoclonal antibodies (mAbs) can have thyroid stimulating activity (TSAb), or can be thyroid blocking antibodies. They are obtainable by genetic immunization of mice against the human TSH receptor (hTSHr), selection of mice scoring positive for the presence of antibodies stimulating or blocking the hTSHr, hybridoma generation using spleen cells of selected mice, and expansion, testing and selection of hybridoma clones producing mAbs having thyroid stimulating or blocking activity. The invention also provides fragments (F(ab')$_2$, Fab or Fv) or humanized forms of such monoclonal antibodies or single chain forms (SCA; scFv) of such fragments.

Antibodies according to the present invention, or their fragments, are characterized by a combination of at least three of the following features:
a. they compete with bovine TSH for epitopes of the human TSHr,
b. they compete with autoantibodies from sera from Graves' patients as well as with autoantibodies from sera from patients harboring blocking autoantibodies for epitopes of the human TSHr,
c. they bind to conformational epitopes of the human TSHr located in the first 281 amino acids of the human TSHr,
d. they bind to TSH receptors (TSHr) of human, mouse, rat, cat, dog and sheep origin, and
e. their dissociation constants $K_d$, when measured in saturation experiments on tubes coated with a recombinant human TSHr preparation, are in the range of about $20\times 10^{-10}$ M to about $0.5\times 10^{-10}$ M.

Stimulating mAbs, i.e. mAbs having thyroid stimulating activity (mTSAb) and behaving as agonists of the human TSHr when tested in media with physiological salt concentrations, preferably
e. either have variable regions of their heavy and light chains respectively which show at least 90% homology with the heavy chains according to SEQ ID NO:1 or SEQ ID NO:9 and/or with the light chains according to SEQ ID NO:2 or SEQ ID NO:10, or
f. are humanized or single chain mAbs or fragments of mAbs containing at least the complementarity determining regions (CDRs) of the heavy chain according to SEQ ID NO:3) SEQ ID NO:4 or SEQ ID NO:11; and SEQ ID NO:5; and/or the complementarity determining regions (CDRs) of the light chain according to SEQ ID NO:6; SEQ ID NO:7 or SEQ ID NO:12; and SEQ ID NO:8 or SEQ ID NO:13.

Blocking mAbs, i.e. mAbs having thyroid blocking activity (mTBAb) and behaving as antagonists of the human TSHr, preferably
g. either have variable regions of their heavy and light chains respectively which show at least 90% homology with the heavy chain according to SEQ ID NO:14 and/or with the light chain according to SEQ ID NO:15, or
h. are humanized or single chain mAbs or fragments of mAbs containing at least the complementarity determining regions (CDRs) of the heavy chain according to SEQ ID NO:16; SEQ ID NO:17 or SEQ ID NO:18; and/or the complementarity determining regions (CDRs) of the light chain according to SEQ ID NO:19; SEQ ID NO:20 or SEQ ID NO:21.

In the application a phrase as "obtainable by genetic immunization of mice against the human TSH receptor (hTSHr), selection of mice scoring positive for the presence of antibodies stimulating (or blocking) the human TSHr (hTSHr), hybridoma generation using spleen cells of selected mice", is, in accordance with established criteria, to be considered as product-by-process feature which does not imply a restriction of the claims, or of the technical teaching, to antibodies which are actually made by said protocol, i.e. by genetic immunization of a mouse. If antibodies obtained by other immunization techniques show all the features recited in the following description, they are to be considered as antibodies of the invention.

Further, the following description, the term "fragments" is intended to mean specifically binding bivalent or monovalent fragments of antibodies according to the invention. A person skilled in the art knows that such fragments can e.g. be F(ab')$_2$ fragments obtainable by digestion of complete antibodies (immunoglobulins) with pepsin, Fab fragments obtainable by digestion of complete antibodies (immunoglobulins) with papain, and fragments produced synthetically or by genetic engineering methods, as e.g. Fv fragments comprising essentially only the complete variable regions of Fab fragments. The term "antibodies" in general is intended to cover also so-called "single chain" antibodies (SAB) or single-chain Fv fragments (scFv) consisting of variable regions of a heavy and a light chain linked by an artificial linker moiety; and "humanized" antibodies in which at least the Fc portion, or even some or all constant regions and/or framework sequences of the variable chains, of a native murine antibody are replaced by corresponding portions or amino acid sequences of corresponding human antibodies. Such humanized antibodies are especially preferred for in vivo uses in humans as therapeutics or adjunctive diagnostics.

Sequences of amino acids, i.e. peptide sequences, are throughout the description described by reference to the enclosed "Sequence Listing" which lists sequences of variable chain regions, and CDRs (complementarity determining regions) of the stimulating mAbs IRI-SAb2, IRI-SAb3 (SEQ ID NO:1 to SEQ ID NO:13) and the blocking antibody 1H7 (SEQ ID NO:14 to SEQ ID NO:21) in accordance with FIG. 5. In case of discrepancies between the Sequence Listing and FIG. 5, the sequences depicted in FIG. 5 are to be considered as the correct sequences.

When numerical values are quoted, they are to be considered as obtained in measurements conducted in accordance with the relevant procedures outlined in the experimental section of the present application.

If the term "agonist" or "full agonist" is used, said terms can be expressed as percentage of the activity (cAMP production) exerted in a bioassay by bovine TSH (saturating concentration) on cells expressing the hTSHr. "Agonist" usually means more than 20%, more usually 40% or more, "full agonist" 80% or more of the activity of bovine TSH.

In the present application the applicants describe the generation of a new series of mAbs, two of which have thyroid stimulating activities and another is a potent blocking antibody. One of the mAbs, in the following named IRI-SAb2, is a full low nanomolar agonist of the TSHr, whose epitope was surprisingly shown to overlap closely with the epitope of the potent blocking antibody named 1H7.

Further, after intravenous injection in mice, IRI-SAb2 caused hyperthyroidism. In addition to histological signs of hyperstimulation, thyroid glands from injected animals displayed signs of infiltration with macrophages and follicular necrosis.

An experimental murine model of Graves' disease was used to produce said novel series of monoclonal antibodies (mAbs) including mAbs with potent thyroid stimulating activity (TSAb). Out of 129 mAbs recognizing the TSH receptor (TSHr), seven displayed TSAb activity. Two of these, named IRI-SAb2 and IRI-SAb3, showed particularly high potency (in the low nanomolar range) and efficacy. IRI-SAb2 behaved as a full agonist of the human TSHr, even when tested in physiological salt concentrations. Both IRI-SAb2 and IRI-SAb3, as well as 1H7, were displaced from the TSHr by autoantibodies from patients with Graves' disease (n=100) or harboring thyroid blocking antibodies (n=8), but not from control subjects (n=104) or patients with Hashimoto thyroiditis (n=20). The epitopes of IRI-SAb2 and IRI-SAb3 were precisely mapped, at the amino acid level, to the aminoterminal portion of the concave portion of the horseshoe structure of TSHr ectodomain. They overlap tightly with each other and, surprisingly, with the epitope of a mAb with blocking activity (1H7). When injected intravenously in mice, both mAbs caused biological and histological signs of hyperthyroidism. Unexpectedly, they triggered also an inflammatory response in the thyroid glands. These new mAbs, with their conformational epitopes delineated, open the way to the identification of the molecular mechanisms implicated in the activation of the TSHr.

In the following the invention is described in more detail by reference to the following non-limiting examples and figures.

IN THE FIGURES

FIG. 1 shows the effect of stimulating mAbs on CAMP accumulation and TSH binding. A and B are concentration action curves of IgG (A) or Fab (B) of IRI-SAb2, IRI-SAb3 and, for comparison, IRI-SAb1 on intracellular cAMP accumulation measured on JP26 cells in normal isotonic salt medium. Results are expressed in pmoles cAMP/ml. 100 mIU/ml bTSH was used to evaluate the maximum stimulation of cAMP production. All measurements were performed in duplicates. C: Effect of various concentrations of IgG of IRI-SAb1, 2 and 3 or mAb 1H7 on inhibition of $^{125}$I-bTSH binding to immobilized hTSHr on coated tubes, as measured by a commercial assay (DYNO-test® TRAK human; B.R.A.H.M.S Aktiengesellschaft, Hennigsdorf, Germany). Results are expressed as $^{125}$I-bTSH bound, in cpm. All measurements were done in triplicates.

FIG. 2 shows the competition between mAbs and patient antibodies for binding to the TSHr. A total of 232 sera was tested for their inhibitory effect on the binding of three novel mAbs, and IRI-TSAb1 for comparison, to the TSHr. Control: 104 control sera from blood donors with no personal or family history of endocrine autoimmune disease. Graves: 100 sera from patients with GD containing TSAb. TBAb: 8 sera from TBAb positive patients with autoimmune hypothyroidism. Hashimotos: 20 sera of patients with autoimmune hypothyroidism without TBAb or TBII. A, B, C and D: IRI-SAb1, 2, 3 and mAb 1H7 respectively, used as tracer. E: Bovine TSH used as tracer (LUMItest® TRAK human, B.R.A.H.M.S Aktiengesellschaft). Results were expressed as percentage inhibition of antibody or bTSH binding. Distribution of autoantibodies is shown as dot plots and box plots, indicating 25-75th percentiles (box) with median (line), 10-90th percentile (whiskers). ***, P c 0.0001 (by Mann-Whitney rank sum analysis).

Figure 3:
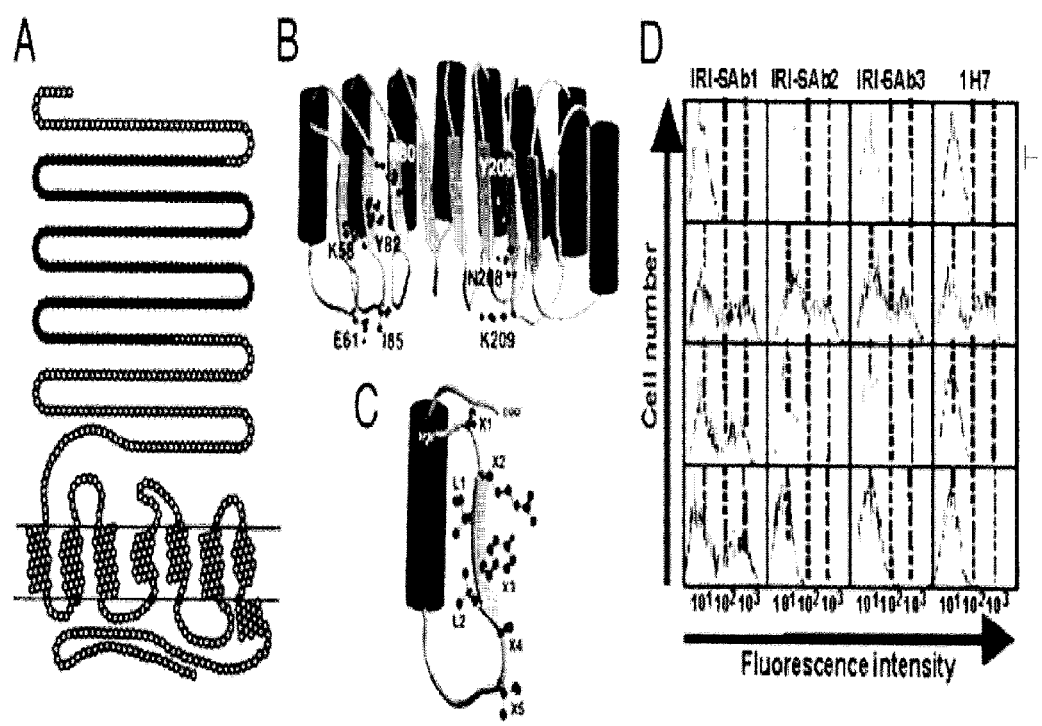

FIG. 3 shows the localization of IRI-SAb2, IRI-SAb3 and 1H7 epitopes. A: Schematic representations of TSHr. The seven transmembrane helices are drawn as helical nets. Closed circles in the N-terminal portion represent the LRR portion of the ectodomain (residues 54-254) B: Schematic representations of the LRR portion of TSHr with the eight residues mutated in chimera T56. C: Schematic representation of a single structural LRR. D: Mapping of the epitopes of IRI-SAb1, 2, 3 and 1H7 with hTSHr mutant transfected in COS cells. T56 is a mutant of TSHr with eight residues mutated (see schematic representation above). T90 is a mutant of TSHr with 20 residues mutated with LHr counterparts. COS cells were transfected with wild type or mutated TSHr, stained with mAbs and analyzed by FACS as described in Material and Methods.

FIG. 4 shows the cartography of IRI-SAb2, IRI-SAb3 and 1H7 epitope: β-strands of the nine LRRs of the TSHr ectodomain. Only the X residues, putatively facing the hormone and the antibodies are represented. Numbering starts from the first amino acid of the signal peptide of the TSHr. Residues implicated in the recognition of TSHr by the antibody were identified individually (in black box), or in combination (surrounded by a dotted box). A: Cartography of the IRI-SAb2 epitope. B: Cartography of the IRI-SAb3 epitope. C: Cartography of the 1H7 epitope.

FIG. 5 shows amino acid sequences of variables regions of IRI-SAb2(VH =SEQ ID NO: 1; VL =SEQ ID NO: 2), IRI-SAb3 (VH =SEQ ID NO: 9; VL =SEQ ID NO: 10) and 1H7(VH =SEQ ID NO: 14; VL =SEQ ID NO: 15); Sequence alignments of variable regions from heavy (VH) and light (VL) chains. CDRs regions are boxed. Amino acids are numbered according to the Kabat nomenclature. In black boxes: the four residues different between IRI-SAb2 and IRI-SAb3.

Figure 6:
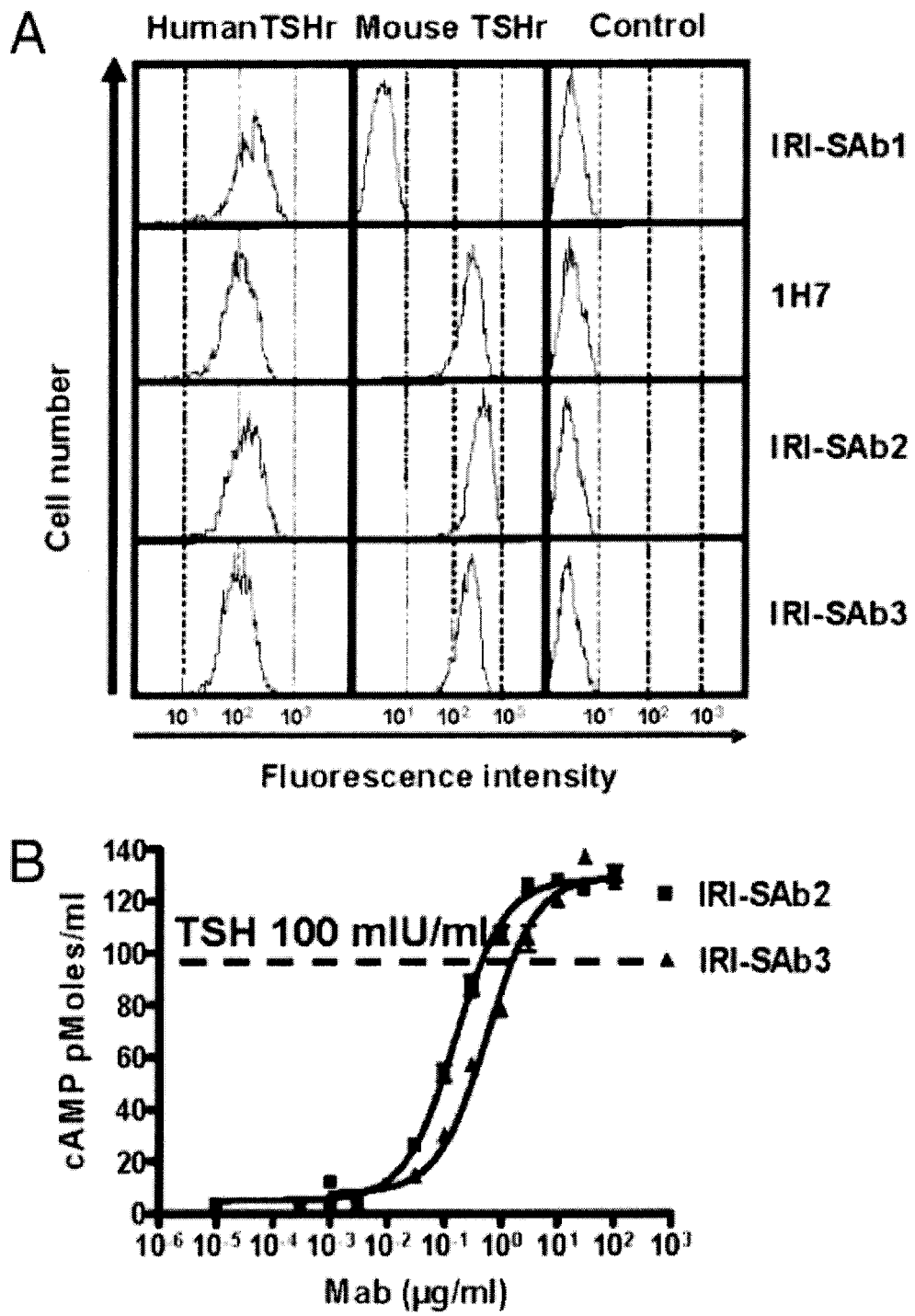

FIG. 6 shows that IRI-SAb2 and 3 stimulate the mouse TSHr in vitro: A: FACS with the four antibodies on MT3 cell line expressing the mouse TSHr. Cells were stained with each antibody and analyzed as described above. B: Concentration action curve of IgGs of IRI-SAb2 and 3 on intracellular cAMP accumulation measured on MT3 cells in normal isotonic salt medium. A concentration action curve was also performed with bovine TSH (data not shown) and the plateau corresponding to the maximum stimulation of cAMP production achieved with 100 mIU/ml bTSH is shown. Results are expressed in pmoles cAMP/ml. All measurements were performed in duplicates.

FIG. 7 Total T4 and TSH in sera from female mice treated with 100 µg of purified IRI-SAb2 and IRI-SAb3. Groups treated with PBS, mAb BA8 or mAb 1H7 were used as control. T4 (µg/dl) and TSH (mIU/L) respectively, 48 hours (A and C) and four days (B and D) post injection. Distribution of values is shown as dot plots, with median (line). **, P<0.01 (by Mann-Whitney rank sum analysis). E. T4 values in mice treated with IRI-SAb2 or PBS (control) 8 hours, 24 hours and 7 days post injection. Due to repeated bleeding, minimum amount of serum was harvested and the TSH values were not evaluated in this experiment.

Further features of the present invention can be derived from the following detailed description of experiments and results.

1. Material and Methods
1.1. Reagents

The 3G4 (15) and BA8 (16) monoclonal antibodies, were described elsewhere. mAb IRI-SAb1, which was more closely investigated for comparison, was also already partially characterized (11). Bovine TSH was purchased from Sigma (Chemical CO, St Louis, Mo.). All primers used for PCR, cloning or sequencing were synthesized by Eurogentec (Seraing, Belgium) and sequences are available upon request.

1.2. Animals Used, Sampling, Hybridomas Generation

Six-week old female NMRI mice [Ico:NMRI (IOPS:Han)] were immunized with cDNA coding for the human TSHr as already described (8). Blood samples were obtained 8 weeks, after the initial immunization. For all determinations sera were tested individually. Mice were handled and housed in accordance with procedures approved by the local committee for animal well-being. Mouse 42, scoring positive for the presence in serum of antibodies stimulating the hTSHr, was selected and fusion of spleen cells with myeloma NS1/0 was performed as previously described (11,16). 1200 clones were expanded in liquid medium after selection in methyl-cellulose HAT medium (ClonCell-HY selective medium, STEMCELL Technologies Inc, Vancouver, Canada).

1.3. Characterization of Antibodies in the Serum of Mouse 42 Selected for Hybridoma Production 1.3.1. Flow Cytometry FACS analysis was performed as previously described (16) with 2 µl of serum on CHO cells expressing the hTSHr [JP19 (17)]. Results are expressed in AFU (arbitrary fluorescence units).

1.3.2. Measurement of TSAb

TSAb activity was measured using CHO cells expressing the hTSHr [JP26 (17)], as described (18). Duplicate samples were assayed in all experiments; results are expressed as pmoles cAMP/ml.

1.3.3. Screening for mAbs with TSAb or TSH Binding Inhibiting Ig (TBII) Activity Supernatants were collected and the presence of antibodies against hTSHr was evaluated using three assays: FACS on JP19 cells with 10 µl of supernatant (see above); Competition for $^{125}$I-TSH binding was performed with DYNOtest® TRAK human coated tubes (B.R.A.H.M.S Aktiengesellschaft, Hennigsdorf) (19) and with 50 µL of supernatant; Stimulation of cAMP production using JP26 CHO cells (see above) with 10 µl of supernatant. Hybridomas scoring positive in the three tests were cloned, expanded and Ig Isotype of mAb was determined (IsoStrip™, Roche, Belgium).

1.4. Characterization of Selected mAbs 1.4.1. TSAb and TBII activities

Selected mAbs and Fabs (generated after papain digestion) were purified by Sepharose-protein A affinity chromatography (ImmunoPure™ Fab preparation Kit, Pierce, Perbio Science, Belgium) and tested for their ability to stimulate cAMP production using JP26 CHO cells in normal isotonic medium (see above). For TBII activity determination, different amounts of antibodies were added in 250 µl of buffer A (20 mM Hepes-NaOH, pH 7.5, 50 mM NaCl, 1% BSA, 10% glycerol, 2 mg/ml mouse IgG) to hTSHr coated tubes. After 1 h incubation at room temperature, 50 µl $^{125}$I-TSH (B.R.A.H.M.S Aktiengesellschaft) in the same buffer were added. The tubes were incubated for 2 h at room temperature, washed four times with 2 ml washing buffer (8 mM Tris-HCl, 60 mM NaCl, 0.02% Tween-20, pH 7.5), and bound radioactivity was counted.

1.4.2. $K_d$ Determination 5 ng (~200 000 RLU) of acridinium ester labelled monoclonal antibody (20) and different amounts of unlabeled antibodies were added in 0.3 ml of buffer A to TSHr coated tubes. Tubes were incubated for 24 h at room temperature, washed four times with 2 ml washing buffer, and RLU were measured in a luminometer.

1.4.3. Competition Between mAbs and Autoantibodies on hTSHr Coated Tubes

150 µl buffer (100 mM Hepes-KOH, pH 7.5, 20 mM EDTA, 0.5 mM N-ethyl-maleimide, 1% BSA, 0.5% Triton X100, 30 µg/ml anti-human TSH antibody, 2 mg/ml mouse IgGs) and 100 µl of patients' sera or standards were added to TSHr coated tubes. After 2 h incubation, 50 µl of PBS containing 5 ng of labelled antibody were added as a tracer. Tubes were incubated overnight at 4° C., washed four times with 2 ml washing buffer, and bound RLU was measured in a luminometer. Results were expressed as inhibition index (InI) calculated as; InI (%)=100−100×(count rate for the test serum/count rate for the standard zero sera). Graves' disease (GD) sera were obtained from blood donors recruited for the development of in vitro diagnostics, which was approved by a national ethical committee. Sera from patients with autoimmune thyroid disease, who were clinically hypothyroid but contained high levels of TBII, were a kind gift from Dr Daphne Khoo (Singapore General Hospital). Written consent was given by all blood donors.

1.4.4. Data Analysis

Concentration-action curves, saturation curves, Scatchard and statistical analysis (by non parametric Mann-Whitney rank sum test) were fitted and computed with the Prism® program (GraphPad Software, Inc., San Diego, Calif., USA).

1.5. In Vivo Assay with Stimulating mAbs

100 µg of purified mAbs (IRI-SAB2, IRI-SAB3, 1H7, BA8) in PBS were injected in the tail vein of 8 weeks old female Balb/c mice. Blood samples were obtained at various times post injection. PBS and mAb BA8 were used as controls.

1.6. Total T4 and TSH Assays

Total T4 was measured with a commercial kit (T4 mAb, ICN pharmaceuticals, New York, USA). TSH was measured as previously described (21).

1.7. Light Microscopy and Immunohistochemistry

Four days post injection with purified mAbs, mice were exsanguinated by cardiac puncture under Nembutal anesthesia. The thyroid glands were removed and processed for light microscopy and immunohistochemistry. Frozen sections were subjected to immunoperoxidase staining using monoclonal antibodies specific for CDR5RA positive immune cells and Mac-1 positive macrophages cells, as previously described (22).

1.8. Variable Region Gene Analysis

Total RNA was isolated with the RNeasy Mini Kit (Qiagen Inc., Valencia, Calif., USA). Following first strand cDNA synthesis with random hexamers, the heavy and light chain Fv regions were amplified using degenerate primers described by Kettleborough et al (23) and sequenced. The sequences were compared with available sequences of mouse Ig genes using IMGT/V-QUEST (http://imgt.cines.fr/textes/vquest/). The replacement/silent R/S mutation ratio was calculated for the framework (FR) and CDR regions of the heavy and light chain. A CDR R/S ratio>2.9 (calculated for somatic mutations occurring randomly in a gene encoding a protein whose structure need not be preserved) is indicative of antigen driven maturation of the antibodies, whereas a lower FR R/S mutation ratio (<2.9) reflects the negative pressure of structural components that need to be conserved (24).

2. Results 2.1. Mouse Selected for the Hybridoma Fusion

Twenty female NMRI mice were immunized against the human TSHr following the protocol of genetic immunization described previously (12). Mice were bled eight weeks after the first DNA injection and antibodies against TSHr were detected by FACS in all sera from immunized mice, with values ranging from 20±2.5 AFU to 91±7 AFU (control values: 6±0.82 AFU). TBII activity was similarly present in all sera from immunized mice, values ranging from 42 to 92% inhibition of labelled TSH binding (control mice: 2±0.5 TSAb activity was detectable in only five sera, with cAMP values higher than 5 pmoles/ml (controls mice: 0.77±0.15 pmoles/ml). Three mice showed total T4 significantly higher than controls (>4.5 µg/dl). Mouse 42, positive in all four assays and displaying the highest values in TBII, TSAb and total T4 was selected for hybridoma fusion.

2.2. Screening and Selection of mAb with TSAb Activity

Out of 1,200 hybridoma which were analyzed, 129 scored positive after screening by FACS on JP19 cells. Thirty of these were positive for TBII in the TRAK assay, out of which seven stimulated cAMP production in the JP26 cells, under incubation in normal-salt medium (see methods). The cAMP values ranged from 9.3±0.2 pmoles/ml to 188.3±8.7 pmoles/ml (control supernatants: 1.49±0.15 pmoles/ml). Out of the seven supernatants displaying TSAb activity, two achieved a stimulation of cAMP production reaching 67% (IRI-SAb2, 188.3±8.7 pmoles/ml, or 126 fold the basal cAMP value) and 20% (IRI-SAb3, 56±1.2 pmoles/ml, or 37 fold the basal cAMP value) of the maximum stimulation caused by a saturating concentration of bovine TSH (100 mIU/ml, 280±21 pmoles/ml). These two mAbs were selected for production, and purified for further analysis. The IgG isotypes were IgG2a for IRI-SAb2 and IgG1 for IRI-SAb3.

2.3. Functional Characterization of IRI-SAb2 and IRI-SAb3

2.3.1. TSAb Activity of IgGs

Various concentrations of purified IRI-SAb2 and IRI-SAb3 were tested for their ability to stimulate cAMP production in JP26 cells incubated in normal salt medium. A concentration-dependent increase in cAMP production was observed in both cases, with maximum stimulations of 131-fold and 105-fold the basal cAMP values for IRI-SAb2 and IRI-SAb3, respectively (FIG. 1A). These values represented 98% and 80%, respectively, of the maximum stimulation generated in the same experiment by a saturating concentration of bovine TSH (100 mIU/ml). $EC_{50}$ were 2.75±0.25 nM and 16.5±3.5 nM for IRI-SAb2 and IRI-SAb3, respectively. By comparison, the maximal stimulation achieved by the previously characterized IRI-SAb1 (11) (EC50=3.6±0.6 nM) was only 10% of the value achieved with bovine TSH (FIG. 1A, inset). These results indicate that under the conditions of the assay, IRI-SAb2 behaves as a full agonist of the hTSHr.

Kinetics of intracellular cAMP accumulation after stimulation of JP26 cells with 30 µg/ml of the three mAbs or with bovine TSH (1 mIU/ml) were similar. 80% of the maximal values were reached in less than 5 min for IRI-SAb1 and after 10-20 min for IRI-SAb2, IRI-SAb3 and TSH. The mean time for achieving 50% of the values reached at 2 h was 4±1 min for IRI-SAb2, 7±1 min for IRI-SAb3 and 5±1 min for TSH (mean±range) (not shown).

2.3.2. TSAb Activity of Fab Fragments

The efficacies of the three mAb Fab fragments on stimulation of cAMP production, were similar to those obtained with the corresponding intact immunoglobulins, with IRI-SAb2 behaving again as a full agonist (FIG. 1B). $EC_{50}$ values were in the same range as those displayed by intact IgGs (1.2±0.5 nM and 74±4 nM for IRI-SAb2 and IRI-SAb3, respectively).

2.3.3. TBII Activity of mAbs

Various concentrations of purified IRI-SAb1, IRI-SAb2 and IRI-SAb3 were incubated with $^{125}$I-labeled TSH on TSHr coated tubes (FIG. 1C). The mAb 1H7, detected in the original screening as blocking the TSH binding but devoid of TSAb activity, was also tested. IRI-SAb2, IRI-SAb3 and 1H7 competed with TSH binding, and the concentrations required to displace 50% of the $^{125}$I-labeled TSH were 2±0.5 nM (0.3±0.075 µg/ml), 3.3±0.2 nM (0.5±0.03 µg/ml), and 2.6±0.2 nM (0.4±0.03 µg/ml), respectively. In contrast, IRI-SAb1 was poorly effective and at 10 µg/ml (66 nM), less than 5 of the $^{125}$I-labeled TSH was displaced.

The purified antibodies were subsequently labelled with acridinium ester and used in saturation experiments on hTSHr coated tubes. The $K_d$ of the previously described mAb IRI-SAb1 was 2×10$^{-8}$ M. The binding affinity of IRI-SAb2, IRI-SAb3 and 1H7 was in the 10$^{-10}$ M range, but biphasic saturation curves were observed ($K_{d1}$: 0.7×10$^{-10}$ M, 2.8× 10$^{-10}$ M, 1.2×10$^{-10}$ M, respectively. $K_{d2}$: 12.3×10$^{-10}$ M, 19.6×10$^{-10}$ M, 13.3×10$^{-10}$ M, respectively). These Kds were similar to that of bovine TSH ($K_{d1}$: 0.2×10$^{-10}$ M, $K_{d2}$: 4.1× 10$^{-10}$ M) (25) and a recently published human monoclonal antibody with TSAb properties ($K_d$: 5×10$^{-18}$ M) (14). The two different dissociation constants exhibited by IRI-SAb2, IRI-Sab3 and 1H7 for the TSHr could be interpreted as reflecting a heterogenous preparation of TSHr (partially denatured) on the coated tubes.

Taking into consideration the apparently varying affinity for the binding to hTSHr preparations, it can be said that the dissociation constants $K_d$ of the novel antibodies according to the present invention, when measured in saturation experiments on tubes coated with a recombinant human TSHr preparation, are in the range of about 20×10$^{-10}$ M to about 0.5×10$^{-10}$ M.

2.3.4. Competition with Sera from Patients with Graves Disease for Binding to TSHr The four mAbs labeled with acridinium ester were used as binding tracers on hTSHr coated tubes (20). Competition was assayed with the sera from 104 euthyroid control subjects, 100 patients with Graves' disease, 8 patients scoring positive in a TSH blocking activity (TBAb) assay, and 20 TBII negative patients with Hashimoto's disease. All these sera were also evaluated in a TSH-TRAK assay (19). Except for IRI-SAb1, all mAbs were efficiently and significantly competed for by autoantibodies from Graves' disease, or TBAb positive patients, when compared to control subjects or Hashimoto's patients (FIG. 2).

2.4. Characterization of Epitopes 2.4.1. IRI-SAb2, IRI-SAb3 and 1H7

IRI-SAb2, IRI-SAb3 and 1H7 antibodies recognized the TSHr from human, mouse, rat, cat dog and sheep, when tested by FACS (data not shown). Chimeras between the TSH receptor and the LH/CG receptor pointed, for all three mAbs, to epitopes located in the first 281 residues of the ectodomain (data not shown). We then tested the ability of these antibodies to interact with residues of the inner surface of the horseshoe region of the TSHr. This surface (FIG. 3A and FIG. 3B) has been shown to be composed of nine units of seven residues, $X_1$-$X_2$-L-$X_3$-L-$X_4$-$X_5$. The side-chains of the X residues are predicted to face the solvent, being available for interaction with the hormones, or antibodies (FIG. 3C). This model has been validated by demonstrating that exchanging specific X residues between the GPHRs resulted in swapping of recognition specificity in the corresponding chimeras (3). The three mAbs did not recognize the T90 chimera, harboring 20 substitutions of X residues (FIG. 3D), nor the T56 chimera, where X residues were mutated at 8 positions (3 residues in the LRR1, 2 residues in LRR2 and 3 residues in LRR7) (FIG. 3B and FIG. 3D). We then tested a total of 35 mutants where X residues where mutated individually, or in combination. The results are compiled on FIG. 4.

The epitope of IRI-SAb2 included a series of nine X residues belonging to LRR1, 2 and 3 (FIG. 4A). Interestingly, except for $I^{60}$ ($X_4$ of LRR1), none of these residues was able to affect recognition of the constructs by the antibody, when mutated in isolation. In contrast the three triple mutants ($X_{2,3,4}$ of LRR1, $X_{2,3,5}$ of LRR2 and $X_{2,3,4}$ of LRR3) were not recognized anymore by IRI-SAb2. Mutations "en bloc" of residues $X_{1,2,3,4,5}$ of LRR4 to 6, did not impair the interaction of IRI-SAb2 with the TSHr.

The epitope of IRI-SAb3 included X residues belonging to LRR1 to LRR6 (FIG. 4B). Contrary to the situation with IRI-SAb2, many residues completely abolished recognition of TSHr by IRI-SAb3 when mutated individually: $I^{60}$ and $E^{61}$ ($X_4$ and $X_5$ of LRR1), $Y^{82}$ and $I^{85}$ ($X_3$ and $X_5$ of LRR2), $E^{107}$ and $R^{109}$ ($X_3$ and $X_4$ of LRR3), $E^{157}$ ($X_3$ of LRR5), and $K^{183}$ ($X_3$ of LRR6). Only in LRR4, was the simultaneous substitution of residues $X_{2,3,4}$ necessary to impair the interaction. Mutations of all $X_{1,2,3,4,5}$ residues of LRR 7, 8 and 9 did not impair the interaction of IRI-SAb3 with the TSHr.

The epitope of mAb 1H7 included X residues belonging to LRR1 to LRR4 (FIG. 4C). Residues which fully impaired the recognition of TSHr when mutated individually were: $T^{56}$ and $K^{58}$ ($X_2$ and $X_3$ of LRR1), $R^{80}$ and $Y^{82}$ ($X_2$ and $X_3$ of LRR2), $R^{109}$ ($X_4$ of LRR3). Similar to the observation with IRI-SAb3, simultaneous mutation of $X_{2,3,4}$ residues of LRR4 was necessary to impair the interaction of 1H7 with TSHr. Mutations, in combination, of residues $X_{1,2,3,4,5}$ of LRR5 and LLR6 were without effect.

2.4.2. IRI-SAb1 (Investigated for Comparison)

FACS results from COS-7 cells transfected with the TSHr of various species, demonstrated that IRI-SAb1 recognizes the human TSHr very efficiently and, to a lesser extent, the sheep receptor. It did not bind to TSHr from rat, cat or dog nor to the mouse receptor. A first analysis of the binding of IRI-SAb1 to a series of chimeras between rat and human TSH receptor pointed to a segment of the ectodomain between positions 21 ($G^{21}$, the first amino acid after the signal peptide) and 165, encompassing the N-terminal cysteine cluster portion and the first half of the horseshoe structured region [containing leucine rich repeats (LRR) one to five]. Alignment of TSHr of various species identified two residues, $Q^{45}$ (located in the N-terminal cysteine cluster region) and $Q^{91}$ (located in the loop between the second β-sheet and the second α-helix of the LRRs region), which were substituted in the TSHr from non-recognized species (by a $H^{45}$ and an $R^{91}$, respectively). When these two "human-specific" residues were introduced in the rat TSHr background, recognition of the chimera was restored. These results indicate that $Q^{45}$ and $Q^{91}$ are most probably part of the epitope of IRI-SAb1. Finally, this antibody was tested by FACS on the T90 chimera (3), in which nearly all the $X_{2,3,4,5}$ residues of the β-strands of the LRRs of the TSHr were exchanged for their LH/CGr counterparts (see ref (3) and FIG. 3C, for details). These amino acid substitutions did not affect recognition by IRI-SAb1, indicating that, in agreement with the binding data (FIG. 1C), the epitope of this antibody does not overlap with the inner surface of the horseshoe region of the TSHr (FIG. 3D).

2.5. Sequence and Structure Analysis of the Variable Regions of IRI-SAb2, IRI-SAb3 and 1H7

The nucleotide sequences of the V genes coding for the different mAbs and the corresponding amino acid sequences were determined (FIG. 5). A high sequence identity is observed between the heavy (93%) and the light chains (91%) of IRI-SAb2 and IRI-SAb3, respectively. mAb 1H7 shared 72-75% identities with IRI-SAB2 or IRI-SAb3 for its heavy chain and 50-52% for the light chain (FIG. 5). A replacement/silent (R/S) mutation ratio>2.9 within the heavy chain CDRs reflected the positive selective pressure of the antigen on these antibodies (24).

IRI-SAb2 and IRI-SAb3 differ only in four CDR residues (FIG. 5). According to Kabat numbering, IRI-SAb2 has $N^{53}$ and $R^{93}$ in the light chain where IRI-SAb3 has $S^{53}$ and $S^{93}$. Two residues in the heavy chain are also variable: $F^{53}$ and $T^{57}$ for IRI-SAb2 and $Y^{53}$ and $A^{57}$ for IRI-SAb3 (FIG. 5). The residues at position, 53 and 93 in the light chain and at position 53 in the heavy chain are located on the surface of the molecule, in the predicted antigen binding region. They could interact with residues from the TSHr and account for the slightly different abilities of IRI-SAb2 and 3 to stimulate the TSHr.

2.6. Biological Activity of IRI-SAb2 and IRI-SAb3 in Mice, Ex Vivo and In Vivo

The ability of the two antibodies to interact with the mouse TSHr was tested, using a CHO cell line (MT3) expressing the murine receptor (unpublished data). While IRI-SAb1 did not bind to the mouse TSHr by FACS (see above), IRI-SAb2, IRI-SAb3 and 1H7 recognized equally well the human and murine receptors (FIG. 6A). These results are in agreement with the data concerning the epitopes. The residues found important in the interaction of the three antibodies are 100% conserved between the human and murine TSHr.

IRI-SAb2 and IRI-SAb3 were then tested for their ability to stimulate the mouse TSHr in normal-salt medium (FIG. 6B). A concentration-dependent increase in cAMP production was observed, with a maximum stimulation of 22 fold the basal cAMP values for the two antibodies. This represented 134% of the maximum stimulation generated in the same experiment by a saturating concentration of bovine TSH. $EC_{50}$ were 1.3±0.66 nM for IRI-SAb2 and 3.8±0.48 nM for IRI-SAb3.

The in vivo stimulating activity of IRI-SAb2 and IRI-SAb3 was then assessed by intravenous injection of IgGs in mice. PBS, mAb BA8 (devoid of biological activity) and mAb 1H7 serving as controls. Two days after injection (FIG. 7A), the total T4 levels were almost double in mice injected with IRI-SAb2 or IRI-SAb3, when compared to the control groups. Out of the 10 mice injected with IRI-SAb2 or IRI-SAb3, nine presented a very low TSH level, below 10 mIU/L. In contrast, TSH levels in the control groups were very heterogeneous: only 2 mice out of the 15 controls showed TSH values below 10 mIU/L (FIG. 7C). In all the mice injected with IRI-SAb2 or IRI-SAb3, T4 levels remained stably high four days post injection (FIG. 7B) and TSH values below 10 mIU/L (FIG. 7D). We subsequently investigated the short and long time responses to TSAb, in a group of mice injected with IRI-SAb2 (FIG. 7E). 8 hours post injection, T4 levels were already elevated (8.18±0.83 µg/dl). These levels decreased slightly at 24 hours and had almost normalized seven days post injection, which is consistent with the reported serum half life of mouse IgG2a (6-8 days).

In these hyperthyroid mice, thyroid morphology was considerably modified as compared to control mice. The follicular epithelial layers were often made of hypertrophic cells, with irregular apical poles protruding into the colloid. Numerous necrotic thyrocytes were also detected, shedded in some follicular lumina, which is considered a sign of a toxic effect of the acute hyperstimulation. Dying thyrocytes, with picnotic eccentric nuclei were also observed in the some follicles. An extended infiltrate throughout the gland was observed. These cells, in the interstitium, were immunohistochemically typed as CD45+ immune cells and numerous Mac-1+ positive macrophages were observed between the thyrocytes and inside the colloid.

2.7 Deposition Under the Budapest Treaty

Hybridomas producing the two stimulating antibodies IRI-SAb2 and IRI-SAb3, and the blocking antibody 1H7, were deposited on May 27, 2004 with DSMZ-Deutsche Sammlung von Mikroorganismen and Zellkulturen. GmbH, Mascheroder Weg 1b, D-38124 Braunschweig and were allotted the Accession Numbers (Eingangsnummern) DSM ACC2664; DSM ACC2662 and DSM ACC2663 respectively. The International Receipt Forms of the International Depositary Authority DSMZ are enclosed.

Discussion

With one notable exception (14), monoclonal antibodies with convincing thyroid stimulating activity have been generated only from murine models of Graves' disease (11-13). This implies that success has been obtained from animals in which tolerance to self has been broken, which, in turn, may explain the low yield of these experiments. Since functional screening of mAbs from hyperthyroid mice is usually made with transfected cells expressing the human receptor, the mAbs identified are expected to recognize epitopes common to mouse and man. Among a series of stimulating and blocking mAbs isolated from mice with experimental Graves' disease, three monoclonal with TSAb activity (IRI-SAb1, IRI-SAb2, IRI-SAb3) and one with blocking activity (ref (11) and present application) have been studied in detail.

Conclusions:

a. IRI-SAb2 is a Full Agonist of the Human TSHr

Although considered to act in the low nanomolar range (25-28), autoantibodies with TSAb activity display a wide range of efficacy in currently used cAMP-based assays. The observation that performing TSAb assays in low-salt media caused significant increase in sensitivity, led people to adopt low-salt conditions to run standard clinical TSAb tests (29). Similarly, the first murine mAbs with TSAb activity were mainly tested in low-salt media (13) and there was no indication about their functioning as full or partial agonists of the human TSHr. A hamster monoclonal antibody was clearly a partial agonist (12). IRI-SAb2 and, to a lesser extent, IRI-SAb3 make exception. When tested under normal salt conditions, their ability to stimulate cAMP accumulation in hTSHr-expressing CHO cells, amounts to 98% and 80% of the maximal stimulation achieved by bTSH, which matches the strongest TSAbs found in rare patients. Coupled with this high efficacy, their potency approaches that of TSH ($EC_{50}$ 2.75±0.25 nM and 16.5±3.5 nM versus 1 nM for bTSH). Binding affinity to the human TSHr of both IRI-SAb2 and IRI-SAb3 match that of autoantibodies purified from Graves' patients (25). In comparison, the previously characterized IRI-SAb1 (FIG. 1A) and mAb MS-1 (12) are weak, partial agonists, which suggest that they do not recognize well the "trigger" epitope. Also, contrary to MS-1 which displays a bell shape concentration-action curve (interpreted as indication for down regulation of the TSHr) (12), IRI-SAb2 and IRI-SAb3 show classidal sigmoid concentration-action curves in semilog plots, with no sign of down-regulation or desensitization at high mAb concentrations (FIG. 1A). A human monoclonal described recently, (14) approaches the functional characteristics of IRI-SAb2. However it remains to be demonstrated whether it behaves as a full agonist of the human TSHr in normal salt medium.

b. Stimulating Activity of IRI-SAb2 and IRI-SAb3 is Preserved in Fab Fragments

Dimerization/oligomerization of GPCRs is a subject of intense current interest. Despite some contradictory indications there is however no strong evidence that modification of the di/oligomerization status of GPCRs or GPCRs is involved in the activation process, per se. Our results with Fab fragments of IRI-SAb2 and IRI-SAb3 confirm earlier results with TSAbs from patients (1,30) that monovalent antibodies are as active as intact IgGs, ruling out that activation by these antibodies would be secondary to forced dimerization or aggregation.

c. Molecular Delineation of Conformational Epitopes of TSAbs: There is More than one Way to Stimulate the TSHr From the first studies, when the cloned TSHr cDNA became available, it was concluded that the epitopes of TSAb from Graves' patients were conformational (1,31-33). This notion is in agreement with the results obtained with the present, as well as previously described mAbs with stimulating activity (12,13). IRI-SAb1 bound only to the human TSHr and its epitope was localized in the N-terminal part of the ectodomain. This epitope involves a glutamine residue ($Q^{45}$), located in the first cysteine cluster of the ectodomain, immediately upstream of the LRR portion. $Q^{45}$ belongs to a segment of the receptor predicted to be highly conformational, and particularly well exposed to the interaction with TSAb in constructs in which the serpentine portion of the TSHr has been replaced by a glycosylphosphatidylinositol anchor. The epitope of IRI-SAb1 contains a second glutamine residue ($Q^{91}$), located on the convex portion of the horseshoe structure of the ectodomain, in the α-helix of the second LRR. This face of the horseshoe is not expected to make direct contact with TSH (3), which is consistent with the absence of TSH-displacing activity of IRI-SAb1 (FIG. 1C). This raises the possibility that some autoantibodies with no TBII activity could act as TSAbs. Although TBII-negative patients with Graves' disease have been described, they are rare, in agreement with the notion that the majority of TSAbs do compete with TSH for binding to the TSHr (19). Consistent with this view, IRI-SAb1 is not'displaced by the vast majority of autoantibodies from Graves' patients (FIG. 2A).

Contrary to IRI-SAb1, monoclonals IRI-SAb2 and IRI-SAb3 according to the present invention are not specific to the human TSHr; they recognize the TSHr from several species, including mouse in which they were generated. Whereas their epitopes were also localized in the N-terminal part of the receptor, contrary to IRI-SAb1, they involve several residues belonging to the β-strands of LRRs. As such, their epitopes map in the concave face of the aminoterminal portion of the horseshoe structure (FIGS. 3 and 4), a region demonstrated as being directly implicated in specific interactions with TSH (3). A detailed comparison, at the single amino acid level, of the epitopes of IRI-SAb2 and IRI-SAb3 demonstrates extensive overlap involving the β-sheets of LRR1,2 and 3 (FIG. 4). Interestingly, the epitope of IRI-SAb3 extends further to residues of LRR4, 5 and 6 (FIG. 4). Considering the weaker efficacy of IRI-SAb3 when compared to IRI-SAb2, this suggests that agonistic activity may depend more on the nature of the interacting residues, rather than on the extend of the interaction surface. Although interpretation of such overlap must be taken with some caution (the amino acid substitutions from which they are inferred may cause long range structural perturbations), these data delineate the β-sheets of LRR1 to 3 as containing an "activation trigger" of TSHr ectodomain. In parallel to this observation, the very limited number of amino acid substitutions in the Fv regions of IRI-SAb2 and IRI-SAb3 predicted to interact with the epitopes (three residues, two in the light chains and one in the heavy chains) (FIG. 5) indicate that the two mAbs originate from a common gene rearrangement. It demonstrates that the difference between partial or full agonistic activity of the antibodies depends on very subtle structural differences. In turn, these observations open the way to the identification of activating interactions of the trigger region, by reciprocal site-directed mutagenesis of the recombinant antibodies and ectodomain constructs.

d. Epitopes of Strong Stimulating and Blocking mAbs do Overlap with Each Other and with Determinants of TSH Binding The epitope of the strong blocking mAb, 1H7, overlaps strikingly with those of IRI-SAb2 and IRI-SAb3. It shares 5 residues with each of them ($T^{56}$, $K^{58}$, $R^{80}$, $Y^{82}$, $R^{109}$ with IRI-SAb2; $Y^{82}$, $R^{109}$, $F^{130}$, $G^{132}$, $F^{134}$ with IRI-SAb3). Again interpretation of such overlap at the single aminoacid level must be taken with caution (see above). Nevertheless, this observation is strong indication that the difference between stimulating and blocking antibodies may involve very similar and close-by epitopes. Functional studies involving mutated constructs of both the ectodomain and recombinant mAbs endowed, or not, with stimulating activity should help delineating residues implicated in the activation trigger. Not surprisingly, the blocking mAb 1H7 is as well displaced from the receptor by autoantibodies from Graves' patients as IRI-SAb2 and IRI-SAb3 (FIG. 2D). This observation is in complete agreement with recent results showing that purified autoantibodies from patients with "pure" blocking activity (i.e. displaying no TSAb activity) cannot be distinguished from purified TSAb for their ability to be displaced from the TSHr by autoantibodies from classical Graves' patients (25). Together, these observations challenge the notion that activating and blocking antibodies would recognize epitopes located in the aminoterminal and carboxylterminal portions of the ectodomain (33, review).

e. IRI-SAb2 and 3 are Effective Stimulators of Murine TSHr Ex Vivo and In Vivo

Their isolation from a mouse displaying signs of thyrotoxicosis suggested strongly that IRI-SAb2 and IRI-SAb3 were responsible for (or contributed to) the hyperthyroid state.

As stated above, this implies that tolerance to self has been broken and that some antibodies in this animal must be able to recognize and activate the murine TSHr. Both IRI-SAb2 and IRI-SAb3 present these characteristics when tested ex vivo on CHO cells expressing the mouse TSHr (FIG. 6). Unexpectedly, both IRI-SAb2 and IRI-SAb3 were stronger agonists than bovine TSH in this assay system (FIG. 6). It is conceivable that they would stabilize more efficiently the active conformation of the ectodomain than bovine TSH, the situation with murine TSH having not been explored.

Also, the difference in efficacy of the two mAbs observed in stimulation of the human TSHr is not observed with the mouse receptor (compare FIG. 1 with FIG. 6).

In agreement with these observations, mice injected intravenously with IRI-SAb2 and IRI-SAb3 displayed biological signs of hyperthyroidism (FIG. 7). The kinetics of the change in plasma total T4 after IRI-SAB2 injection, was grossly compatible with the known half-lives of the mouse IgG2a isotype (34), with no sign of acute desensitization (FIG. 7E). The histology of the glands, four days after injection of either IRI-SAb2 or IRI-SAb3, displays the expected signs of thyrocyte hyperstimulation. Unexpectedly, however, it also revealed acute signs of inflammation and toxicity, with numerous infiltrating macrophages and dying cells desquamated in the colloid spaces. This picture could be interpreted as the consequence of an acute stimulation of the TSHr, inducing overproduction of $H_2O_2$ at the apical membrane, followed by an inflammatory process. The ability of a purely humoral stimulation by TSAbs to cause an inflammatory reaction in the glands of non immunized mice is interesting in the context of the pathophysiology of Graves' disease. According to common knowledge the inflammatory signs of thyroid tissue observed in Graves' disease are the consequence of an ongoing autoimmune reaction, maintained by local antigens. Our results suggest that overstimulation per se may contribute importantly to the inflammatory picture. Future studies, in which IRI-SAb2 and IRI-SAb3 will be administered chronically to naive mice, will show whether overstimulation of the glands may, by itself, lead to an autoimmune reaction with generation of anti-thyroglobulin and/or anti-thyroperoxidase autoantibodies.

Perspectives:

As already noted, the monoclonal antibodies described in the present application constitute promising novel tools to probe the molecular mechanisms implicated in the activation of the TSHr.

Variable regions of these mAbs can be cloned and, in contrast with TSH, easily produced as recombinant material. Both the CDR regions of the antibodies and the LRR portion of the receptor can be modified by site-directed mutagenesis and tested in functional assays. This should open the way to the identification of interacting residues in the two partners which, in turn, may provide hints about the conformational changes associated with the activation mechanisms.

From a clinical point of view, monoclonal antibodies with biological activity are increasingly used in various fields of medicine (35). With their high potency and efficacy, their long half life and expected lower production cost, IRI-SAb2 and IRI-SAb3 (or humanized derivatives thereof) may be seen as an interesting alternative to recombinant TSH for various in vivo protocols in man. These include stimulation of thyroid remnants or metastasis, in patients with differentiated thyroid cancer before measurement of serum thyroglobulin and whole-body scan with $I^{131}$ (36) or administration of therapeutic doses of $I^{131}$. Accordingly, the present invention, according to one of its aspects, also relates to the use of mAbs of the present invention, or fragments or humanized or single chain forms thereof, in unlabeled form or labeled with a detectable marker or a radioisotope, for the preparation of therapeutic medicaments or diagnostic compositions and agents for in vivo diagnostics and imaging purposes.

Blocking mAb 1H7 is of interest as a potential alternative for a use (therapeutical method) in the treatment of hyperthyroidism in accordance with DE 199 07 094 C1 and corresponding WO 00/49050 A2/A3. Accordingly, the present invention also covers the use of such blocking mAb for the preparation of a medicament for treating hyperthyroidism.

In addition, their high affinity for binding to the human TSHr may qualify IRI-SAb2 and IRI-SAb3, as well as 1H7, as tracers in in vitro immunoassays or with application in the imaging or, linked to a radiolabel or a cytotoxic agent or toxine, for the destruction especially of non-iodine uptaking metastases of less differentiated thyroid cancers.

Peptides corresponding to variable regions, or to CDRs, of the novel mAbs can be used for testing purposes, as immunogens and in affinity purification.

LIST OF REFERENCES

1. Rapoport, B., Chazenbalk, G. D., Jaume, J. C., and McLachlan, S. M. 1998. The thyrotropin (TSH) receptor: interaction with TSH and autoantibodies. *Endocr. Rev.* 19:673-716.
2. Szkudlinski, M. W., Fremont, V., Ronin, C., and Weintraub, B. D. 2002. Thyroid-stimulating hormone and thyroid-stimulating hormone receptor structure-function relationships. *Physiol Rev.* 82:473-502.
3. Smits, G., Campillo, M., Govaerts, C., Janssens, V., Richter, C., Vassart, G., Pardo, L., and Costagliola, S. 2003. Glycoprotein hormone receptors: determinants in leucine-rich repeats responsible for ligand specificity. *EMBO J.* 22:2692-2703.
4. Kajava, A. V., Vassart, G., and Wodak, S. J. 1995. Modeling of the three-dimensional structure of proteins with the typical leucine-rich repeats. *Structure.* 3:867-877.
5. Weetman, A. P. 2000. Graves' Disease. *N Engl J Med* 343:1236-1248.

6. Prabhakar, B. S., Bahn, R. S., and Smith, T. J. 2003. Current perspective on the pathogenesis of Graves' disease and ophthalmopathy. *Endocr. Rev.* 24:802-835.
7. Shimojo, N., Kohno, Y., Yamaguchi, K., Kikuoka, S., Hoshioka, A., Niimi, H., Hirai, A., Tamura, Y., Saito, Y., Kohn, L. D. et al. 1996. Induction of Graves-like disease in mice by immunization with fibroblasts transfected with the thyrotropin receptor and a class II molecule. *Proc. Natl. Acad. Sci. U.S.A.* 93:11074-11079.
8. Costagliola, S., Many, M. C., Denef, J. F., Pohlenz, J., Refetoff, S., and Vassart, G. 2000. Genetic immunization of outbred mice with thyrotropin receptor cDNA provides a model of Graves' disease. *J. Clin. Invest* 105:803-811.
9. Nagayama, Y., Kita-Furuyama, M., Ando, T., Nakao, K., Mizuguchi, H., Hayakawa, T., Eguchi, K., and Niwa, M. 2002. A novel murine model of Graves' hyperthyroidism with intramuscular injection of adenovirus expressing the thyrotropin receptor. *J. Immunol.* 168:2789-2794.
10. Rao, P. V., Watson, P. F., Weetman, A. P., Carayanniotis, G., and Banga, J. P. 2003. Contrasting activities of thyrotropin receptor antibodies in experimental models of Graves' disease induced by injection of transfected fibroblasts or deoxyribonucleic acid vaccination. *Endocrinology* 144:260-266.
11. Costagliola, S., Franssen, J. D., Bonomi, M., Urizar, E., Willnich, M., Bergmann, A., and Vassart, G. 2002. Generation of a mouse monoclonal TSH receptor antibody with stimulating activity. *Biochem. Biophys. Res. Commun.* 20; 299:891-896.
12. Ando, T., Latif, R., Pritsker, A., Moran, T., Nagayama, Y., and Davies, T. F. 2002. A monoclonal thyroid-stimulating antibody. *J. Clin. Invest* 110:1667-1674.
13. Sanders, J., Jeffreys, J., Depraetere, H., Richards, T., Evans, M., Kiddie, A., Brereton, K., Groenen, M., Oda, Y., Furmaniak, J. et al. 2002. Thyroid-stimulating monoclonal antibodies. *Thyroid* 12:1043-1050.
14. Sanders, J., Evans, M., Premawardhana, K. E., Depraetere, H., Jeffreys, J., Richards, T., Furmaniak, J., and Rees Smith, B. 2003. Human monoclonal thyroid stimulating autoantibody. *The Lancet* 362:126-128.
15. Costagliola, S., Khoo, D., and Vassart, G. 1998. Production of bioactive amino-terminal domain of the thyrotropin receptor via insertion in the plasma membrane by a glycosylphosphatidylinositol anchor. *FEBS Lett* 436:427-433.
16. Costagliola, S., Rodien, P., Many, M. C., Ludgate, M., and Vassart, G. 1998. Genetic immunization against the human thyrotropin receptor causes thyroiditis and allows production of monoclonal antibodies recognizing the native receptor. *J. Immunol.* 160:1458-1465.
17. Perret, J., Ludgate, M., Libert, F., Gerard, C., Dumont, J. E., Vassart, G., and Parmentier, M. 1990. Stable expression of the human TSH receptor in CHO cells and characterization of differentially expressing clones. *Biochem. Biophys. Res. Commun.* 171:1044-1050.
18. Van Sande, J., Lejeune, C., Ludgate, M., Munro, D. S., Vassart, G., Dumont, J. E., and Mockel, J. 1992. Thyroid stimulating immunoglobulins, as thyrotropin, activate both the cyclic AMP and PIP2 cascades in CHO cells expressing the TSH receptor. *Mol. Cell Endocrinol.* 88:R1-R5.
19. Costagliola, S., Morgenthaler, N. G., Hoermann, R., Badenhoop, K., Struck, J., Freitag, D., Poertl, S., Weglohner, W., Hollidt, J. M., Quadbeck, B. et al. 1999. Second generation assay for thyrotropin receptor antibodies has superior diagnostic sensitivity for Graves' disease. *J. Clin. Endocrinol. Metab.* 84:90-97.
20. Minich, W. B., Lenzner, C., and Morgenthaler, N. G. 2004. Antibodies to TSH-receptor in thyroid autoimmune disease interact with monoclonal antibodies whose epitopes are broadly distributed on the receptor. *Clin Exp. Immunol.* 136:129-136.
21. Weiss, R. E., Forrest, D., Pohlenz, J., Cua, K., Curran, T., and Refetoff, S. 1997. Thyrotropin regulation by thyroid hormone in thyroid hormone receptor β-deficient mice. *Endocrinology* 138:3624-3629.
22. Costagliola, S., Many, M. C., Stalmans Falys, M., Tonacchera, M., Vassart, G., and Ludgate, M. 1994. Recombinant thyrotropin receptor and the induction of autoimmune thyroid disease in BALB/c mice: a new animal model. *Endocrinology* 135:2150-2159.
23. Kettleborough, C. A., Saldanha, J., Ansell, K. H., and Bendig, M. M. 1993. Optimization of primers for cloning libraries of mouse immunoglobulin genes using the polymerase chain reaction. *Eur. J. Immunol.* 23:206-211.
24. Jukes, T. H. and King, J. L. 1979. Evolutionary nucleotide replacements in DNA. *Nature* 281:605-606.
25. Morgenthaler, N. G., Minich, W. B., Willnich, M., Bogusch, T., Hollidt, J. M., Weglohner, W., Lenzner, C., and Bergmann, A. 2003. Affinity purification and diagnostic use of TSH receptor autoantibodies from human serum. *Molecular and Cellular Endocrinology* 212:73-79.
26. Chazenbalk, G. D., Wang, Y., Guo, J., Hutchison, J. S., Segal, D., Jaume, J. C., McLachlan, S. M., and Rapoport, B. 1999. A Mouse Monoclonal Antibody to a Thyrotropin Receptor Ectodomain Variant Provides Insight into the Exquisite Antigenic Conformational Requirement, Epitopes and in Vivo Concentration of Human Autoantibodies. *Journal of Clinical Endocrinology Metabolism* 84:702-710.
27. Cornelis, S., Uttenweiler-Joseph, S., Panneels, V., Vassart, G., and Costagliola, S. 2001. Purification and characterization of a soluble bioactive amino-terminal extracellular domain of the human thyrotropin receptor. *Biochemistry* 40:9860-9869.
28. Jaume, J. C., Kakinuma, A., Chazenbalk, G. D., Rapoport, B., and McLachlan, S. M. 1997. Thyrotropin receptor autoantibodies in serum are present at much lower levels than thyroid peroxidase autoantibodies: analysis by flow cytometry. *J. Clin. Endocrinol. Metab* 82:500-507.
29. Kasagi, K., Hidaka, A., Hatabu, H., Lu, C., Misaki, T., Iida, Y., and Konishi, J. 1989. Mechanisms of increased sensitivity for detection of thyroid stimulating antibodies by use of hypotonic medium. *Acta Endocrinol. Copenh.* 121:216-222.
30. Rees Smith, B., McLachlan, S. M., and Furmaniak, J. 1988. Autoantibodies to the thyrotropin receptor. *Endocr. Rev.* 9:106-121.
31. Libert, F., Lefort, A., Gerard, C., Parmentier, M., Perret, J., Ludgate, M., Dumont, J. E., and Vassart, G. 1989. Cloning, sequencing and expression of the human thyrotropin (TSH) receptor: evidence for binding of autoantibodies. *Biochem. Biophys. Res. Commun.* 165:1250-1255.
32. Nagayama, Y., Kaufman, K. D., Seto, P., and Rapoport, B. 1989. Molecular cloning, sequence and functional expression of the cDNA for the human thyrotropin receptor. *Biochem. Biophys. Res. Commun.* 165:1184-1190.
33. Rapoport, B. and McLachlan, S. 2000. Thyroid Autoantibodies in Graves' disease. In Graves' Disease Pathogenesis and Treatment. B. Rapoport and McLachlan, S., editors. Kluwer Academic Publishers, Boston. 43-66.
34. Vieira, P. and Rajewsky, K. 1988. The half-lives of serum immunoglobulins in adult mice. *Eur. J. Immunol.* 18:313-316.
35. Gura, T. 2002. Therapeutic antibodies: Magic bullets hit the target. *Nature* 417:584-586.

36. Pacini, F., Molinaro, E., Castagna, M. G., Agate, L., Elisei, R., Ceccarelli, C., Lippi, F., Taddei, D., Grasso, L., and Pinchera, A. 2003. Recombinant Human Thyrotropin-Stimulated Serum Thyroglobulin Combined with Neck Ultrasonography Has the Highest Sensitivity in Monitoring Differentiated Thyroid Carcinoma. *Journal of Clinical Endocrinology Metabolism* 88:3668-3673.

The invention claimed is:

1. An antibody produced by a hybridoma cell deposited under the Budapest Treaty on May 27, 2004 with DSMZ, Braunschweig under the name 1H7 (DSM ACC2663).

2. A hybridoma cell deposited under the Budapest Treaty on May 27, 2004 with DSMZ Braunschwig and designated DSM ACC2663.

\* \* \* \* \*

```
                         SEQUENCE LISTING

<160> NUMBER OF SEQ ID NOS: 30

<210> SEQ ID NO 1
<211> LENGTH: 97
<212> TYPE: PRT
<213> ORGANISM: Homo sapiens

<400> SEQUENCE: 1

Ser Cys Lys Ala Ser Gly Tyr Ser Phe Thr Ala Tyr Thr Met Asn Trp
1               5                   10                  15

Val Lys Gln Ser His Gly Lys Asn Leu Glu Trp Ile Gly Leu Ile Asn
            20                  25                  30

Pro Phe Asn Gly Gly Thr Asn Tyr Asn Gln Lys Phe Glu Gly Lys Ala
        35                  40                  45

Thr Leu Thr Val Asp Lys Ser Ser Thr Thr Ala Tyr Met Glu Leu Leu
    50                  55                  60

Ser Leu Thr Ser Glu Asp Ser Ala Val Tyr Tyr Cys Ala Arg Arg Val
65                  70                  75                  80

Trp Asp Tyr Phe Asp Tyr Trp Gly Gln Gly Thr Ser Leu Thr Val Ser
                85                  90                  95

Ser

<210> SEQ ID NO 2
<211> LENGTH: 84
<212> TYPE: PRT
<213> ORGANISM: Homo sapiens

<400> SEQUENCE: 2

Glu Gly Ser Ile Thr Cys Lys Ala Ser Gln Asn Val Gly Thr Asn Val
1               5                   10                  15

Ala Trp Tyr Gln Gln Lys Gly Gly Gln Ser Leu Glu Leu Leu Ile Tyr
            20                  25                  30

Gly Ala Ser Asn Arg His Thr Gly Val Pro Asp Arg Phe Thr Gly Arg
        35                  40                  45

Gly Ser Gly Thr Asp Phe Thr Leu Thr Ile Thr Asn Val Gln Ser Glu
    50                  55                  60

Asp Met Thr Asn Tyr Phe Cys Glu Gln Tyr Ser Arg Tyr Pro Leu Thr
65                  70                  75                  80

Phe Gly Ala Gly

<210> SEQ ID NO 3
<211> LENGTH: 12
<212> TYPE: PRT
<213> ORGANISM: Artifical sequence
<220> FEATURE:
<221> NAME/KEY: misc_feature
<222> LOCATION: (1)..(12)
<223> OTHER INFORMATION: synthetic peptide

<400> SEQUENCE: 3

Ala Ser Gly Tyr Ser Phe Thr Ala Tyr Thr Met Asn
1               5                   10

<210> SEQ ID NO 4
<211> LENGTH: 13
```

```
<212> TYPE: PRT
<213> ORGANISM: Artifical sequence
<220> FEATURE:
<221> NAME/KEY: misc_feature
<222> LOCATION: (1)..(13)
<223> OTHER INFORMATION: synthetic peptide

<400> SEQUENCE: 4

Leu Ile Asn Pro Phe Asn Gly Gly Thr Asn Tyr Asn Gln
1               5                   10

<210> SEQ ID NO 5
<211> LENGTH: 9
<212> TYPE: PRT
<213> ORGANISM: Artifical sequence
<220> FEATURE:
<221> NAME/KEY: misc_feature
<222> LOCATION: (1)..(9)
<223> OTHER INFORMATION: synthetic peptide

<400> SEQUENCE: 5

Arg Val Trp Asp Tyr Phe Asp Tyr Trp
1               5

<210> SEQ ID NO 6
<211> LENGTH: 10
<212> TYPE: PRT
<213> ORGANISM: Artifical sequence
<220> FEATURE:
<221> NAME/KEY: misc_feature
<222> LOCATION: (1)..(10)
<223> OTHER INFORMATION: synthetic peptide

<400> SEQUENCE: 6

Ala Ser Gln Asn Val Gly Thr Asn Val Ala
1               5                   10

<210> SEQ ID NO 7
<211> LENGTH: 7
<212> TYPE: PRT
<213> ORGANISM: Artifical sequence
<220> FEATURE:
<221> NAME/KEY: misc_feature
<222> LOCATION: (1)..(7)
<223> OTHER INFORMATION: synthetic peptide

<400> SEQUENCE: 7

Gly Ala Ser Asn Arg His Thr
1               5

<210> SEQ ID NO 8
<211> LENGTH: 9
<212> TYPE: PRT
<213> ORGANISM: Artifical sequence
<220> FEATURE:
<221> NAME/KEY: misc_feature
<222> LOCATION: (1)..(9)
<223> OTHER INFORMATION: synthetic peptide

<400> SEQUENCE: 8

Glu Gln Tyr Ser Arg Tyr Pro Leu Thr
1               5

<210> SEQ ID NO 9
<211> LENGTH: 97
<212> TYPE: PRT
<213> ORGANISM: Homo sapien

<400> SEQUENCE: 9
```

Ser Cys Lys Ala Ser Gly Tyr Ser Phe Thr Ala Tyr Thr Met Asn Trp
1               5                   10                  15

Val Lys Gln Ser His Gly Tyr Asn Leu Glu Trp Ile Gly Leu Ile Asn
                20                  25                  30

Pro Tyr Asn Gly Gly Ala Asn Tyr Asn Gln Lys Phe Lys Gly Lys Ala
            35                  40                  45

Thr Leu Thr Val Asp Lys Ser Ser Thr Ala Tyr Met Glu Leu Leu
    50                  55                  60

Ser Leu Thr Ser Glu Asp Ser Ala Val Tyr Tyr Cys Ala Arg Arg Val
65                  70                  75                  80

Trp Asp Tyr Phe Asp Tyr Trp Gly Gln Gly Thr Thr Leu Thr Val Ser
                85                  90                  95

Ser

<210> SEQ ID NO 10
<211> LENGTH: 84
<212> TYPE: PRT
<213> ORGANISM: Homo sapien

<400> SEQUENCE: 10

Glu Gly Ser Ile Thr Cys Lys Ala Ser Gln Asn Val Gly Thr Asn Val
1               5                   10                  15

Ala Trp Tyr Gln Gln Lys Val Gly Gln Ser Leu Glu Leu Leu Ile Tyr
                20                  25                  30

Gly Ala Ser Ser Arg His Thr Gly Val Pro Asp Arg Phe Thr Gly Ser
            35                  40                  45

Gly Ser Gly Thr Asp Phe Thr Leu Thr Ile Thr Asp Val Gln Ser Glu
    50                  55                  60

Asp Met Thr Asn Tyr Phe Cys Glu Gln Tyr Ser Ser Tyr Pro Leu Thr
65                  70                  75                  80

Phe Gly Ala Gly

<210> SEQ ID NO 11
<211> LENGTH: 13
<212> TYPE: PRT
<213> ORGANISM: Artifical sequence
<220> FEATURE:
<221> NAME/KEY: misc_feature
<222> LOCATION: (1)..(13)
<223> OTHER INFORMATION: synthetic peptide

<400> SEQUENCE: 11

Leu Ile Asn Pro Tyr Asn Gly Gly Ala Asn Tyr Asn Gln
1               5                   10

<210> SEQ ID NO 12
<211> LENGTH: 7
<212> TYPE: PRT
<213> ORGANISM: Artifical sequence
<220> FEATURE:
<221> NAME/KEY: misc_feature
<222> LOCATION: (1)..(7)
<223> OTHER INFORMATION: synthetic peptide

<400> SEQUENCE: 12

Gly Ala Ser Ser Arg His Thr
1               5

<210> SEQ ID NO 13
<211> LENGTH: 9

```
<212> TYPE: PRT
<213> ORGANISM: Artifical sequence
<220> FEATURE:
<221> NAME/KEY: misc_feature
<222> LOCATION: (1)..(9)
<223> OTHER INFORMATION: synthetic peptide

<400> SEQUENCE: 13

Glu Gln Tyr Ser Ser Tyr Pro Leu Thr
1               5

<210> SEQ ID NO 14
<211> LENGTH: 99
<212> TYPE: PRT
<213> ORGANISM: Homo sapien

<400> SEQUENCE: 14

Ser Cys Lys Thr Ser Gly Tyr Thr Phe Thr Ser Tyr Trp Met His Trp
1               5                   10                  15

Val Lys Gln Arg Pro Gly Gln Gly Leu Glu Trp Ile Gly Glu Ile Asp
            20                  25                  30

Pro Ser Asp Ser Tyr Ser Asn Tyr Asn Gln Lys Phe Lys Gly Lys Ala
        35                  40                  45

Thr Leu Thr Val Asp Lys Ser Ser Thr Ala Tyr Met Gln Leu Ser
    50                  55                  60

Ser Leu Thr Ser Glu Asp Ser Ala Val Tyr Tyr Cys Ala Arg Asn Tyr
65                  70                  75                  80

Gly Ser Gly Tyr Tyr Phe Asp Tyr Trp Gly Gln Gly Thr Thr Leu Thr
                85                  90                  95

Val Ser Ser

<210> SEQ ID NO 15
<211> LENGTH: 83
<212> TYPE: PRT
<213> ORGANISM: Homo sapien

<400> SEQUENCE: 15

Lys Val Thr Met Thr Cys Ser Ala Ser Ser Val Ser Tyr Met His
1               5                   10                  15

Trp Tyr Gln Gln Lys Ser Gly Thr Ser Pro Lys Arg Trp Ile Tyr Asp
            20                  25                  30

Thr Ser Lys Leu Ala Ser Gly Val Pro Ala Arg Phe Ser Gly Ser Gly
        35                  40                  45

Ser Gly Thr Ser Tyr Ser Leu Thr Ile Ser Ser Met Glu Ala Glu Asp
    50                  55                  60

Ala Ala Thr Tyr Tyr Cys Gln Gln Trp Ser Ser Asn Pro Tyr Thr Phe
65                  70                  75                  80

Gly Gly Gly

<210> SEQ ID NO 16
<211> LENGTH: 12
<212> TYPE: PRT
<213> ORGANISM: Artifical sequence
<220> FEATURE:
<221> NAME/KEY: misc_feature
<222> LOCATION: (1)..(12)
<223> OTHER INFORMATION: synthetic peptide

<400> SEQUENCE: 16

Thr Ser Gly Tyr Thr Phe Thr Ser Tyr Trp Met His
1               5                   10
```

<210> SEQ ID NO 17
<211> LENGTH: 13
<212> TYPE: PRT
<213> ORGANISM: Artifical sequence
<220> FEATURE:
<221> NAME/KEY: misc_feature
<222> LOCATION: (1)..(13)
<223> OTHER INFORMATION: synthetic peptide

<400> SEQUENCE: 17

Glu Ile Asp Pro Ser Asp Ser Tyr Ser Asn Tyr Asn Gln
1               5                   10

<210> SEQ ID NO 18
<211> LENGTH: 11
<212> TYPE: PRT
<213> ORGANISM: Artifical sequence
<220> FEATURE:
<221> NAME/KEY: misc_feature
<222> LOCATION: (1)..(11)
<223> OTHER INFORMATION: synthetic peptide

<400> SEQUENCE: 18

Asn Tyr Gly Ser Gly Tyr Tyr Phe Asp Tyr Trp
1               5                   10

<210> SEQ ID NO 19
<211> LENGTH: 9
<212> TYPE: PRT
<213> ORGANISM: Artifical sequence
<220> FEATURE:
<221> NAME/KEY: misc_feature
<222> LOCATION: (1)..(9)
<223> OTHER INFORMATION: synthetic peptide

<400> SEQUENCE: 19

Ala Ser Ser Ser Val Ser Tyr Met His
1               5

<210> SEQ ID NO 20
<211> LENGTH: 7
<212> TYPE: PRT
<213> ORGANISM: Artifical sequence
<220> FEATURE:
<221> NAME/KEY: misc_feature
<222> LOCATION: (1)..(7)
<223> OTHER INFORMATION: synthetic peptide

<400> SEQUENCE: 20

Asp Thr Ser Lys Leu Ala Ser
1               5

<210> SEQ ID NO 21
<211> LENGTH: 9
<212> TYPE: PRT
<213> ORGANISM: Artifical sequence
<220> FEATURE:
<221> NAME/KEY: misc_feature
<222> LOCATION: (1)..(9)
<223> OTHER INFORMATION: synthetic peptide

<400> SEQUENCE: 21

Gln Gln Trp Ser Ser Asn Pro Tyr Thr
1               5

<210> SEQ ID NO 22
<211> LENGTH: 7

```
<212> TYPE: PRT
<213> ORGANISM: Artifical sequence
<220> FEATURE:
<221> NAME/KEY: misc_feature
<222> LOCATION: (1)..(7)
<223> OTHER INFORMATION: synthetic peptide

<400> SEQUENCE: 22

Gln Thr Leu Lys Leu Ile Glu
1               5

<210> SEQ ID NO 23
<211> LENGTH: 7
<212> TYPE: PRT
<213> ORGANISM: Artifical sequence
<220> FEATURE:
<221> NAME/KEY: misc_feature
<222> LOCATION: (1)..(7)
<223> OTHER INFORMATION: synthetic peptide

<400> SEQUENCE: 23

Ser Arg Leu Tyr Leu Ser Ile
1               5

<210> SEQ ID NO 24
<211> LENGTH: 7
<212> TYPE: PRT
<213> ORGANISM: Artifical sequence
<220> FEATURE:
<221> NAME/KEY: misc_feature
<222> LOCATION: (1)..(7)
<223> OTHER INFORMATION: synthetic peptide

<400> SEQUENCE: 24

Thr His Leu Glu Leu Arg Asn
1               5

<210> SEQ ID NO 25
<211> LENGTH: 7
<212> TYPE: PRT
<213> ORGANISM: Artifical sequence
<220> FEATURE:
<221> NAME/KEY: misc_feature
<222> LOCATION: (1)..(7)
<223> OTHER INFORMATION: synthetic peptide

<400> SEQUENCE: 25

Lys Phe Leu Gly Leu Phe Asn
1               5

<210> SEQ ID NO 26
<211> LENGTH: 7
<212> TYPE: PRT
<213> ORGANISM: Artifical sequence
<220> FEATURE:
<221> NAME/KEY: misc_feature
<222> LOCATION: (1)..(7)
<223> OTHER INFORMATION: synthetic peptide

<400> SEQUENCE: 26

Phe Ile Leu Glu Leu Thr Asp
1               5

<210> SEQ ID NO 27
<211> LENGTH: 7
<212> TYPE: PRT
<213> ORGANISM: Artifical sequence
<220> FEATURE:
<221> NAME/KEY: misc_feature
```

-continued

```
<222> LOCATION: (1)..(7)
<223> OTHER INFORMATION: synthetic peptide

<400> SEQUENCE: 27

Leu Thr Leu Lys Leu Tyr Asn
1               5

<210> SEQ ID NO 28
<211> LENGTH: 7
<212> TYPE: PRT
<213> ORGANISM: Artifical sequence
<220> FEATURE:
<221> NAME/KEY: misc_feature
<222> LOCATION: (1)..(7)
<223> OTHER INFORMATION: synthetic peptide

<400> SEQUENCE: 28

Asp Ala Leu Tyr Leu Asn Lys
1               5

<210> SEQ ID NO 29
<211> LENGTH: 7
<212> TYPE: PRT
<213> ORGANISM: Artifical sequence
<220> FEATURE:
<221> NAME/KEY: misc_feature
<222> LOCATION: (1)..(7)
<223> OTHER INFORMATION: synthetic peptide

<400> SEQUENCE: 29

Ser Leu Leu Asp Leu Ser Gln
1               5

<210> SEQ ID NO 30
<211> LENGTH: 7
<212> TYPE: PRT
<213> ORGANISM: Artifical sequence
<220> FEATURE:
<221> NAME/KEY: misc_feature
<222> LOCATION: (1)..(7)
<223> OTHER INFORMATION: synthetic peptide

<400> SEQUENCE: 30

Lys Glu Leu Ile Leu Arg Asn
1               5
```